(12) United States Patent
Howard et al.

(10) Patent No.: US 9,077,022 B2
(45) Date of Patent: Jul. 7, 2015

(54) LITHIUM-ION BATTERY

(75) Inventors: William G. Howard, Roseville, MN (US); Craig L. Schmidt, Eagan, MN (US); Erik R. Scott, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 732 days.

(21) Appl. No.: 12/961,319

(22) Filed: Dec. 6, 2010

(65) Prior Publication Data

US 2011/0133699 A1 Jun. 9, 2011

Related U.S. Application Data

(60) Continuation-in-part of application No. 12/510,857, filed on Jul. 28, 2009, now Pat. No. 7,858,236, which is a division of application No. 10/979,041, filed on Oct. 29, 2004, now Pat. No. 7,582,387, application No. 12/961,319, which is a continuation-in-part of application No. 12/564,818, filed on Sep. 22, 2009, now Pat. No. 7,883,790, which is a division of application No. 10/978,970, filed on Oct. 29, 2004, now Pat. No. 7,641,992.

(51) Int. Cl.

| | |
|---|---|
| *H01M 4/131* | (2010.01) |
| *H01M 4/485* | (2010.01) |
| *H01M 4/505* | (2010.01) |
| *H01M 10/0525* | (2010.01) |
| *H01M 10/0569* | (2010.01) |
| *H01M 4/62* | (2006.01) |
| *H01M 10/0568* | (2010.01) |
| *A61N 1/378* | (2006.01) |
| *H01M 4/525* | (2010.01) |
| *H01M 4/587* | (2010.01) |
| *H01M 4/66* | (2006.01) |
| *H01M 10/42* | (2006.01) |

(52) U.S. Cl.
CPC .......... *H01M 4/131* (2013.01); *H01M 10/0569* (2013.01); *H01M 4/625* (2013.01); *H01M 4/623* (2013.01); *H01M 10/0568* (2013.01); *A61N 1/378* (2013.01); *H01M 4/485* (2013.01); *H01M 4/505* (2013.01); *H01M 4/525* (2013.01); *H01M 4/587* (2013.01); *H01M 4/661* (2013.01); *H01M 10/0525* (2013.01); *H01M 10/4235* (2013.01); *Y02E 60/122* (2013.01)

(58) Field of Classification Search
CPC ..... H01M 4/131; H01M 4/485; H01M 4/505; H01M 4/525; H01M 4/587; H01M 4/661; H01M 4/623; H01M 4/625; H01M 10/0525; H01M 10/0569; H01M 10/0568; Y02E 60/122
USPC ........ 429/231.1, 231.3, 231.5, 232, 233, 245, 429/338, 217
See application file for complete search history.

(56) References Cited

U.S. PATENT DOCUMENTS

| | | |
|---|---|---|
| 3,308,306 A | 3/1967 | Bagno |
| 3,462,303 A | 8/1969 | Reber |
| 3,791,867 A | 2/1974 | Broadhead et al. |
| 3,864,167 A | 2/1975 | Broadhead et al. |
| 3,898,096 A | 8/1975 | Heredy et al. |
| 4,009,052 A | 2/1977 | Whittingham |
| 4,048,397 A | 9/1977 | Rothbauer |
| 4,049,887 A | 9/1977 | Whittingham |
| 4,113,921 A | 9/1978 | Goldstein et al. |
| 4,194,062 A | 3/1980 | Carides et al. |
| 4,202,702 A | 5/1980 | Nuss |
| 4,340,652 A | 7/1982 | Raistrick et al. |
| 4,446,212 A | 5/1984 | Kaun |
| 4,464,447 A | 8/1984 | Lazzari et al. |
| 4,507,371 A | 3/1985 | Thackeray et al. |
| 4,547,442 A | 10/1985 | Besenhard et al. |
| 4,555,456 A | 11/1985 | Kanehori et al. |
| 4,581,122 A | 4/1986 | Hammond et al. |
| 4,668,595 A | 5/1987 | Yoshino et al. |
| 4,764,437 A | 8/1988 | Kaun |
| 4,830,939 A | 5/1989 | Lee et al. |
| H723 H | 1/1990 | Plichta et al. |
| 5,053,297 A | 10/1991 | Yamahira et al. |
| 5,077,151 A | 12/1991 | Yasuda et al. |

(Continued)

FOREIGN PATENT DOCUMENTS

| | | |
|---|---|---|
| DE | 19836651 A1 | 2/2000 |
| EP | 0 732 761 A2 | 9/1996 |
| EP | 0 982 790 A1 | 3/2000 |
| EP | 1 014 465 A1 | 6/2000 |
| EP | 1 018 773 A1 | 7/2000 |
| EP | 1 069 635 A1 | 1/2001 |
| EP | 0 567 149 B1 | 11/2001 |
| EP | 1 267 111 A1 | 12/2002 |
| EP | 1 282 180 A1 | 2/2003 |
| EP | 1 487 039 A1 | 12/2004 |

(Continued)

OTHER PUBLICATIONS

Ariyoshi et al., Three-Volt Lithium-Ion Battery with Li[Ni1/2Mn3/2]O4 and the Zero-Strain Insertion Material of Li[Li1/3Ti5/3]O4, Journal of Power Sources, 2003, 5 pages.

(Continued)

*Primary Examiner* — Laura Weiner
(74) *Attorney, Agent, or Firm* — Foley & Lardner LLP

(57) ABSTRACT

A lithium-ion battery includes a positive electrode, a negative electrode, and a battery case. The positive electrode includes a positive current collector, a first material of the form $Li_{1-x}MO_2$, where M is a metal, and a second material including carbon. The negative electrode includes a negative current collector, a third material including a lithium titanate material, and a fourth material including carbon. The battery case includes titanium and at least partially surrounds the positive and negative electrodes.

11 Claims, 16 Drawing Sheets

(56) References Cited

U.S. PATENT DOCUMENTS

| | | |
|---|---|---|
| 5,147,737 A | 9/1992 | Post et al. |
| 5,147,739 A | 9/1992 | Beard |
| 5,160,712 A | 11/1992 | Thackeray et al. |
| 5,162,170 A | 11/1992 | Miyabayashi et al. |
| 5,162,178 A | 11/1992 | Ohsawa et al. |
| 5,169,736 A | 12/1992 | Bittihn et al. |
| 5,176,969 A | 1/1993 | Miyabayashi et al. |
| 5,187,033 A | 2/1993 | Koshiba |
| 5,187,035 A | 2/1993 | Miyabayashi et al. |
| 5,196,279 A | 3/1993 | Tarascon |
| 5,264,201 A | 11/1993 | Dahn et al. |
| 5,284,721 A | 2/1994 | Beard |
| 5,296,318 A | 3/1994 | Gozdz et al. |
| 5,300,373 A | 4/1994 | Shackle |
| 5,322,746 A | 6/1994 | Wainwright |
| 5,331,268 A | 7/1994 | Patino et al. |
| 5,340,666 A | 8/1994 | Tomantschger et al. |
| 5,401,598 A | 3/1995 | Miyabayashi et al. |
| 5,411,537 A | 5/1995 | Munshi et al. |
| 5,418,090 A | 5/1995 | Koksbang et al. |
| 5,478,668 A | 12/1995 | Gozdz |
| 5,498,489 A | 3/1996 | Dasgupta et al. |
| 5,510,212 A | 4/1996 | Delnick et al. |
| 5,525,441 A | 6/1996 | Reddy et al. |
| 5,545,468 A | 8/1996 | Koshiba et al. |
| 5,547,785 A | 8/1996 | Yumiba et al. |
| 5,569,553 A | 10/1996 | Smesko et al. |
| 5,576,608 A | 11/1996 | Nagai et al. |
| 5,652,072 A | 7/1997 | Lamanna et al. |
| 5,670,862 A | 9/1997 | Lewyn |
| 5,691,081 A | 11/1997 | Krause et al. |
| 5,744,258 A | 4/1998 | Bai et al. |
| 5,744,264 A | 4/1998 | Barker |
| 5,776,628 A | 7/1998 | Kraft et al. |
| 5,851,696 A | 12/1998 | Saidi et al. |
| 5,882,218 A | 3/1999 | Reimers |
| 5,888,665 A | 3/1999 | Bugga et al. |
| 5,891,592 A | 4/1999 | Mao et al. |
| 5,911,947 A | 6/1999 | Mitchell |
| 5,935,724 A | 8/1999 | Spillman et al. |
| 5,935,728 A | 8/1999 | Spillman et al. |
| 5,968,681 A | 10/1999 | Miura et al. |
| 6,001,139 A | 12/1999 | Asanuma et al. |
| 6,001,507 A | 12/1999 | Ono et al. |
| 6,007,947 A | 12/1999 | Mayer |
| 6,022,643 A | 2/2000 | Lee et al. |
| 6,025,093 A | 2/2000 | Herr |
| 6,060,186 A | 5/2000 | Broussely |
| 6,067,474 A | 5/2000 | Schulman et al. |
| 6,120,938 A | 9/2000 | Atsumi et al. |
| 6,139,815 A | 10/2000 | Atsumi et al. |
| 6,165,638 A | 12/2000 | Spillman et al. |
| 6,165,646 A | 12/2000 | Takada et al. |
| 6,171,729 B1 | 1/2001 | Gan et al. |
| 6,203,947 B1 | 3/2001 | Peled et al. |
| 6,203,994 B1 | 3/2001 | Epps et al. |
| 6,207,327 B1 | 3/2001 | Takada et al. |
| 6,221,531 B1 | 4/2001 | Vaughey et al. |
| 6,228,536 B1 | 5/2001 | Wasynczuk |
| 6,258,473 B1 | 7/2001 | Spillman et al. |
| 6,265,100 B1 | 7/2001 | Saaski et al. |
| 6,274,271 B1 | 8/2001 | Koshiba et al. |
| 6,287,721 B1 | 9/2001 | Xie et al. |
| 6,316,145 B1 | 11/2001 | Kida et al. |
| 6,335,115 B1 | 1/2002 | Meissner |
| 6,352,798 B1 | 3/2002 | Lee et al. |
| 6,365,301 B1 | 4/2002 | Michot et al. |
| 6,372,384 B1 | 4/2002 | Fujimoto et al. |
| 6,379,841 B1 | 4/2002 | Potanin et al. |
| 6,379,842 B1 | 4/2002 | Mayer |
| 6,451,480 B1 | 9/2002 | Gustafson et al. |
| 6,453,198 B1 | 9/2002 | Torgerson et al. |
| 6,461,751 B1 | 10/2002 | Boehm et al. |
| 6,461,757 B1 | 10/2002 | Sasayama et al. |
| 6,475,673 B1 | 11/2002 | Yamawaki et al. |
| 6,489,062 B1 | 12/2002 | Watanabe et al. |
| 6,503,662 B1 | 1/2003 | Hamamoto et al. |
| 6,528,208 B1 | 3/2003 | Thackeray et al. |
| 6,553,263 B1 | 4/2003 | Meadows et al. |
| 6,596,439 B1 | 7/2003 | Tsukamoto et al. |
| 6,603,146 B1 | 8/2003 | Hata et al. |
| 6,605,382 B2 | 8/2003 | Ruth et al. |
| 6,641,953 B2 * | 11/2003 | Takeuchi et al. .......... 429/231.1 |
| 6,645,670 B2 | 11/2003 | Gan |
| 6,645,675 B1 | 11/2003 | Munshi |
| 6,670,071 B2 | 12/2003 | Skinlo et al. |
| 6,673,493 B2 | 1/2004 | Gan et al. |
| 6,677,083 B2 | 1/2004 | Suzuki et al. |
| 6,706,445 B2 | 3/2004 | Barker et al. |
| 6,720,112 B2 | 4/2004 | Barker et al. |
| 6,730,437 B2 | 5/2004 | Leising et al. |
| 6,732,384 B2 | 5/2004 | Scott |
| 6,737,191 B2 | 5/2004 | Gan et al. |
| 6,759,168 B2 | 7/2004 | Yamasaki et al. |
| 6,761,744 B1 | 7/2004 | Tsukamoto et al. |
| 6,777,132 B2 | 8/2004 | Barker et al. |
| 6,824,920 B1 * | 11/2004 | Iwamoto et al. .......... 429/218.1 |
| 6,841,304 B2 * | 1/2005 | Michot et al. ................ 429/324 |
| 6,849,360 B2 | 2/2005 | Marple |
| 6,869,724 B2 | 3/2005 | Suzuki et al. |
| 6,905,795 B2 | 6/2005 | Jung et al. |
| 6,905,796 B2 | 6/2005 | Ishida et al. |
| 6,908,711 B2 * | 6/2005 | Fauteux et al. ............ 429/231.5 |
| 6,942,949 B2 | 9/2005 | Besenhard et al. |
| 6,946,218 B2 | 9/2005 | Crouch, Jr. et al. |
| 6,951,576 B1 | 10/2005 | Takeuchi |
| 7,018,743 B2 | 3/2006 | Guidi et al. |
| 7,029,793 B2 | 4/2006 | Nakagawa et al. |
| 7,101,642 B2 | 9/2006 | Tsukamoto et al. |
| 7,157,185 B2 | 1/2007 | Marple |
| 7,177,691 B2 | 2/2007 | Meadows et al. |
| 7,184,836 B1 | 2/2007 | Meadows et al. |
| 7,191,008 B2 | 3/2007 | Schmidt et al. |
| 7,202,000 B2 | 4/2007 | Iriyama et al. |
| 7,211,350 B2 | 5/2007 | Amatucci |
| 7,238,449 B2 | 7/2007 | Suzuki et al. |
| 7,337,010 B2 | 2/2008 | Howard et al. |
| 7,341,803 B2 | 3/2008 | Huang et al. |
| 7,392,117 B2 | 6/2008 | Bilodeau et al. |
| 7,459,235 B2 | 12/2008 | Choi et al. |
| 7,462,425 B2 | 12/2008 | Takami et al. |
| 7,488,553 B2 | 2/2009 | Tsukamoto et al. |
| 7,524,580 B1 | 4/2009 | Birke et al. |
| 7,541,114 B2 | 6/2009 | Ohzuku et al. |
| 7,563,541 B2 | 7/2009 | Howard et al. |
| 7,582,380 B1 | 9/2009 | Dunstan et al. |
| 7,582,387 B2 | 9/2009 | Howard et al. |
| 7,632,603 B2 | 12/2009 | Tsukamoto et al. |
| 7,635,541 B2 | 12/2009 | Scott et al. |
| 7,641,992 B2 | 1/2010 | Howard et al. |
| 7,642,013 B2 | 1/2010 | Howard et al. |
| 7,662,515 B2 | 2/2010 | Inagaki et al. |
| 7,682,745 B2 | 3/2010 | Howard et al. |
| 7,740,985 B2 | 6/2010 | Howard et al. |
| 7,794,869 B2 | 9/2010 | Howard et al. |
| 7,799,470 B2 | 9/2010 | Cho et al. |
| 7,803,481 B2 | 9/2010 | Howard et al. |
| 7,807,299 B2 | 10/2010 | Howard et al. |
| 7,811,703 B2 | 10/2010 | Fujita et al. |
| 7,811,705 B2 | 10/2010 | Scott et al. |
| 7,818,068 B2 | 10/2010 | Meadows et al. |
| 7,858,236 B2 | 12/2010 | Howard et al. |
| 7,875,389 B2 | 1/2011 | Scott et al. |
| 7,883,790 B2 | 2/2011 | Howard et al. |
| 7,927,742 B2 | 4/2011 | Scott et al. |
| 2001/0008725 A1 | 7/2001 | Howard |
| 2001/0012590 A1 | 8/2001 | Ehrlich |
| 2001/0021472 A1 | 9/2001 | Barker et al. |
| 2001/0031401 A1 | 10/2001 | Yamawaki et al. |
| 2003/0025482 A1 | 2/2003 | Tsukamoto et al. |
| 2003/0104282 A1 | 6/2003 | Xing et al. |
| 2003/0124423 A1 | 7/2003 | Sasaki et al. |
| 2003/0129485 A1 | 7/2003 | Guidi et al. |
| 2003/0157410 A1 | 8/2003 | Jarvis et al. |

(56) References Cited

U.S. PATENT DOCUMENTS

| | | |
|---|---|---|
| 2003/0190531 A1 | 10/2003 | Otsuki et al. |
| 2003/0215716 A1 | 11/2003 | Suzuki et al. |
| 2004/0002005 A1 | 1/2004 | Gao et al. |
| 2004/0023117 A1 | 2/2004 | Imachi et al. |
| 2004/0029156 A1 | 2/2004 | Matson et al. |
| 2004/0062989 A1 | 4/2004 | Ueno et al. |
| 2004/0072072 A1 | 4/2004 | Suzuki et al. |
| 2004/0096745 A1 | 5/2004 | Shibano et al. |
| 2004/0147971 A1 | 7/2004 | Greatbatch et al. |
| 2004/0147972 A1 | 7/2004 | Greatbatch et al. |
| 2004/0158296 A1 | 8/2004 | Greatbatch et al. |
| 2004/0168307 A1 | 9/2004 | Hong |
| 2004/0176818 A1 | 9/2004 | Wahlstrand et al. |
| 2004/0197657 A1 | 10/2004 | Spitler et al. |
| 2004/0209156 A1 | 10/2004 | Ren et al. |
| 2005/0031919 A1 | 2/2005 | Ovshinsky et al. |
| 2005/0069777 A1 | 3/2005 | Takami et al. |
| 2005/0130043 A1 | 6/2005 | Gao et al. |
| 2005/0147889 A1 | 7/2005 | Ohzuku et al. |
| 2005/0164082 A1 | 7/2005 | Kishi et al. |
| 2005/0244716 A1 | 11/2005 | Ogawa et al. |
| 2006/0024582 A1 | 2/2006 | Li et al. |
| 2006/0046149 A1 | 3/2006 | Yong et al. |
| 2006/0068282 A1 | 3/2006 | Kishi et al. |
| 2006/0090962 A1 | 5/2006 | McGehee |
| 2006/0091572 A1 | 5/2006 | Santra et al. |
| 2006/0093871 A1 | 5/2006 | Howard et al. |
| 2006/0093872 A1 | 5/2006 | Howard et al. |
| 2006/0093873 A1 | 5/2006 | Howard et al. |
| 2006/0093894 A1 | 5/2006 | Scott et al. |
| 2006/0093913 A1 | 5/2006 | Howard et al. |
| 2006/0093916 A1 | 5/2006 | Howard et al. |
| 2006/0093917 A1 | 5/2006 | Howard et al. |
| 2006/0093918 A1 | 5/2006 | Howard et al. |
| 2006/0093921 A1* | 5/2006 | Scott et al. ............... 429/231.1 |
| 2006/0093923 A1 | 5/2006 | Howard et al. |
| 2006/0095094 A1 | 5/2006 | Howard et al. |
| 2006/0216612 A1 | 9/2006 | Jambunathan et al. |
| 2006/0234125 A1 | 10/2006 | Valle |
| 2006/0243598 A1 | 11/2006 | Singh et al. |
| 2006/0251968 A1 | 11/2006 | Tsukamoto et al. |
| 2007/0009801 A1 | 1/2007 | Inagaki et al. |
| 2007/0059587 A1 | 3/2007 | Kishi et al. |
| 2007/0072085 A1 | 3/2007 | Chen et al. |
| 2007/0077496 A1 | 4/2007 | Scott et al. |
| 2007/0111099 A1 | 5/2007 | Nanjundaswamy et al. |
| 2007/0134556 A1 | 6/2007 | Sano et al. |
| 2007/0135662 A1 | 6/2007 | Nardello et al. |
| 2007/0162083 A1 | 7/2007 | Schmidt et al. |
| 2007/0233195 A1 | 10/2007 | Wahlstrand et al. |
| 2007/0239221 A1 | 10/2007 | Kast et al. |
| 2007/0248881 A1 | 10/2007 | Scott et al. |
| 2007/0284159 A1 | 12/2007 | Takami et al. |
| 2008/0020278 A1 | 1/2008 | Schmidt et al. |
| 2008/0020279 A1 | 1/2008 | Schmidt et al. |
| 2008/0026297 A1 | 1/2008 | Chen et al. |
| 2008/0044728 A1 | 2/2008 | Schmidt et al. |
| 2008/0176142 A1* | 7/2008 | Inagaki et al. ............ 429/231.5 |
| 2008/0241689 A1 | 10/2008 | Takami et al. |
| 2009/0035662 A1 | 2/2009 | Scott et al. |
| 2009/0075166 A1 | 3/2009 | Takami et al. |
| 2009/0208834 A1 | 8/2009 | Ramasubramanian et al. |
| 2009/0274849 A1 | 11/2009 | Scott et al. |
| 2009/0286158 A1 | 11/2009 | Howard et al. |
| 2010/0239908 A1 | 9/2010 | Howard et al. |
| 2010/0279155 A1 | 11/2010 | Scott et al. |
| 2010/0316898 A1 | 12/2010 | Howard et al. |

FOREIGN PATENT DOCUMENTS

| | | |
|---|---|---|
| EP | 1 722 439 A1 | 11/2006 |
| JP | 56136462 A | 10/1981 |
| JP | 57011476 | 1/1982 |
| JP | 57152669 A | 9/1982 |
| JP | 02309568 | 12/1990 |
| JP | H05-166538 | 7/1993 |
| JP | 06275263 | 9/1994 |
| JP | 10027626 A | 1/1998 |
| JP | 10-208748 | 8/1998 |
| JP | 2000156229 | 6/2000 |
| JP | 2000195499 A | 7/2000 |
| JP | 2001126756 A | 5/2001 |
| JP | 2001143702 A | 5/2001 |
| JP | 2001185141 A | 7/2001 |
| JP | 2001-210324 | 8/2001 |
| JP | 2001-513679 | 9/2001 |
| JP | 2004-010520 | 1/2004 |
| JP | 2004-296256 A | 10/2004 |
| WO | WO9706569 A1 | 2/1997 |
| WO | WO9748141 A1 | 12/1997 |
| WO | WO 00/17950 A1 | 3/2000 |
| WO | WO 01/33656 A1 | 5/2001 |
| WO | WO 02/09215 A2 | 1/2002 |
| WO | WO 0221628 A1 | 3/2002 |
| WO | WO 0239524 A1 | 5/2002 |
| WO | WO 02/069414 A2 | 9/2002 |
| WO | WO 02/095845 A1 | 11/2002 |
| WO | WO-03/044880 A1 | 5/2003 |
| WO | WO-03/075371 A2 | 9/2003 |
| WO | WO-03/090293 A2 | 10/2003 |
| WO | WO 2004/010520 A1 | 1/2004 |
| WO | WO-2006/050022 A2 | 5/2006 |
| WO | WO-2006/050023 A2 | 5/2006 |
| WO | WO-2006/050098 A1 | 5/2006 |
| WO | WO-2006/050099 A1 | 5/2006 |
| WO | WO-2006/050100 A2 | 5/2006 |
| WO | WO-2006/050117 A2 | 5/2006 |
| WO | WO-2006/064344 A2 | 6/2006 |

OTHER PUBLICATIONS

Battery Materials, Ceramic Anode Material for 2.4 V Lithium-Ion Batteries, Oct. 25, 2004, 1 page.

Belharouak et al., On the Safety of the Li4Ti5O12/LiMn2O4 Lithium-Ion Battery System, Journal of the Electrochemical Society, vol. 154, 2007, 5 pages.

Brohan et al., Properties Physiques Des Bronzes MxTiO2(B), Solid State Ionics, vols. 9 and 10, 1983, 6 pages.

Cava et al., The Crystal Structures of the Lithium-Inserted Metal Oxides Li0.5TiO2 Anatase, LiTi2O4 Spinel, and Li2Ti2O4, Journal of Solid State Chemistry, vol. 53, 1984, 12 pages.

Christensen et al., Optimization of Lithium Titanate Electrodes for High-Power Cells, Journal of the Electrochemical Society, vol. 153, 2006, 6 pages.

Colbow et al., Structure and Electrochemistry of the Spinel Oxides LiTi2O4 and Li4/3Ti5/3O4, Journal of Power Sources 26, 1989, 6 pages.

Dahn et al., Combinatorial Study of Sn1—xCox (0<x<0.6) and [Sn0.55Co0.45]1—yCy (0<y<0.5) Alloy Negative Electrode Materials for Li-Ion Batteries, Journal of Electrochemical Society, vol. 153, 2006, 5 pages.

Fauteux et al., Rechargeable Lithium Battery Anodes: Alternatives to Metallic Lithium, Journal of Applied Electrochemistry, vol. 23, 1993, 10 pages.

Ferg et al., Spinel Anodes for Lithium-Ion Batteries, J. Electrochem. Soc. 141, Nov. 1994, 4 pages.

FMC Lithium, CAS No. 7439-93-2, Stabilized Lithium Metal Powder, Product Specification, 2001 2 pages.

Guerfi et al., Nano Electronically Conductive Titanium-Spinel as Lithium Ion Storage Negative Electrode, Journal of Power Sources, 126, 2004, 6 pages.

Guyomard et al., New Amorphous Oxides as High Capacity Negative Electrodes for Lithium 6 Batteries the LixMV04 (M=Ni, Co, Cd, Zn; 1 <x<8) Series, Journal of Power Sources 68, 1997, 6 pages.

Jansen et al., Development of A High-Power Lithium-Ion Battery, Journal of Power Sources, 81-82, 1999, 4 pages.

Jarvis et al., A Li-Ion Cell Containing A Non-Lithiated Cathode, Abs. 182, IMLB 12 Meeting, 2004, 1 page.

Kavan et al., Proof of Concept—Li4Ti5O12, Electrochemical and Solid State Letters, 2002, vol. 5, 1 page.

(56) References Cited

OTHER PUBLICATIONS

Linden, Handbook of Batteries, 1995, 6 pages.
Medtronic Activa® Product Family and Procedure Solution Product Specifications, 2003, 6 pages.
Medtronic Neurostimulation Systems Product Brochure, 2002, 6 pages.
Mikula et al., Photoelectrochemical Properties of Anodic TiO2 Layers Prepared by Various Current Densities, J. Electrochemical Society, vol. 139, Dec. 1992, 5 pages.
Murphy et al., Topochemical Reactions of Rutile Related Structures with Lithium, Mat. Res. Bull, vol. 13, 8 pages.
Murphy et al., Lithium Insertion in Anatase: A New Route to the Spinel LiTi2O4, Revue De Chimie Minerale, vol. 19, 1982, 5 pages.
Murphy et al., Ternary LixTiO2 Phases from Insertion Reactions, Solid State Ionics, vols. 9 and 10, 1983, 5 pages.
Nakahara et al., Preparation of Particulate Li4Ti5O12 Having Excellent Characteristics as an Electrode Active Material for Power Storage Cells, Journal of Power Sources, 117, 2003, 6 pages.
New Li4Ti5O12 Anode Material of Süd-Chemie AG for Lithium Ion Batteries, Süd-Chemie EXM 1037-Li4Ti5O12 , Product Specification, 2 pages.
Ohzuku et al, Zero-Strain Insertion Material of Li[Li1/3Ti5/3]O4 for Rechargeable Lithium Cells, J. Electrochem. Soc. vol. 142, 1995, 5 pages.
Ohzuku et al., Why Transition Metal (Di)oxides are the Most Attractive Materials for Batteries, Solid State Ionics, vol. 69, 1994, 11 pages.
Ohzuku et al., Lithium-Ion Batteries of Li[Li1/3Ti5/3]O4 With Selected Positive-Electrode Materials for Long-Life Power Application, Abs. 23, IMLB 12 Meeting, 1 page.
Ohzuku, Extended Abstracts from the Seventh Int'l Meeting on Li Batteries, May 15-20, 1994, 3 pages.
Peramunage et al., Preparation of Micro-Sized Li4Ti5O12 and Its Electrochemistry in Polyacrylonitrile Electrolye-Based Lithium Cells, Technical Papers, Electrochemical Science and Technology, J. Electrochem Soc., vol. 145, No. 8, Aug. 1998 © The Electrochemical Society, Inc., 8 pages.
Poizot et al., Nano-Sized Transition-Metal Oxides as Negative-Electrode Materials for Lithium-ion Batteries, Nature, vol. 407, 2000, 5 pages.
Prosini et al., Li4Ti5O12 As Anode in All-Solid-State, Plastic, Lithium-Ion Batteries for Low-Power Applications, Solid State Ionics 144, 2001, 8 pages.
Sasaki et al., Layered Hydrous Titanium Dioxide: Potassium Ion Exchange and Structural Characterization, Inorganic Chemistry, vol. 24, 1985, 4 pages.
Sawai et al., Factors Affecting Rate Capability of a Lithium-ion Battery with Li[Li1/3Ti5/3]O4 and LiCo1/2Ni1/2O2, Abs. 75, 2004, 3 pages.
Scrosati et al, Low Voltage Lithium-Ion Cells, Advances in Lithium-Ion Batteries, Kluwer Academic/Plenum Publishers, 21 pages.
Singhal et al., Nanostructured Electrodes for Next Generation Rechargeable Electrochemical Devices, Journal of Power Sources, 129, 2004, 7 pages.
Sun et al., Using a Boron-Based Anion Receptor Additive to Improve the Thermal Stability of LiPF6-Based Electrolyte for Lithium Batteries, Electrochemical and Solid-State Letters, 2002,, 4 pages.
Sun et al., The Compatibility of a Boron-Based Anion Receptor with the Carbon Anode in Lithium-Ion Batteries, Electrochemical and Solid-State Letters 6, 2003, 4 pages.
Trifonova et al., Sn—Sb and Sn—Bi Alloys as Anode Materials for Lithium-Ion Batteries, Ionics, vol. 8, 2002, 9 pages.
Wang et al. Novel Electrolytes for Nanocrystalline Li4Ti5O12 Based High Power Lithium Ion Batteries, 1 page.
Wang et al., Li Insertion and Ion Exchange Reactions in the Ionic Conducting Tl2(M,Ti)8O16 Phases with Hollandite-Type Structure, J. Electrochem Soc., vol. 138, No. 1, Jan. 1991, 7 pages.
Winter et al., Insertion Electrode Materials for Rechargeable Lithium Batteries, Advanced Materials, vol. 10, 1998, 41 pages.
Winter et al., Electrochemical Lithiation of Tin and Tin-Based Intermetallics and Composites, Electrochimica Acta, vol. 45, 1999, 10 pages.
Zaghib et al., Electrochemical Study of Li4Ti5O12 as Negative Electrode for Li-Ion Polymer Rechargeable Batteries, Journal of Power Sources, 81-82, 1999, 6 pages.
Restriction Requirement for U.S. Appl. No. 12/564,818, mail date Feb. 3, 2010, 8 pages.
Restriction Response for U.S. Appl. No. 12/564,818, mail date Mar. 3, 2010, 9 pages.
Office Action for U.S. Appl. No. 12/564,818, mail date Jun. 17, 2010, 10 pages.
Amendment and Reply, Declaration Under 1.131, Terminal Disclaimer for U.S. Appl. No. 12/564,818, mail date Sep. 15, 2010, 21 pages.
Notice of Allowance for U.S. Appl. No. 12/564,818, mail date Nov. 29, 2010, 8 pages.
Restriction Requirement for U.S. Appl. No. 10/978,722, mail date Dec. 14, 2006, 6 pages.
Amendment and Reply for U.S. Appl. No. 10/978,722, mail date Jan. 16, 2007, 12 pages.
Office Action for U.S. Appl. No. 10/978,722, mail date Mar. 29, 2007, 12 pages.
Amendment and Reply for U.S. Appl. No. 10/978,722, mail date Jul. 30, 2007, 15 pages.
Office Action for U.S. Appl. No. 10/978,722, mail date Oct. 9, 2007, 6 pages.
Request for Continued Examination (RCE), Reply and Declaration Under 1.131 for U.S. Appl. No. 10/978,722, mail date Jan. 9, 2008, 28 pages.
Office Action for U.S. Appl. No. 10/978,722, mail date Mar. 14, 2008, 9 pages.
Request for Continued Examination (RCE), Amendment and Reply and 1.131 Declaration for U.S. Appl. No. 10/978,722, mail date Jul. 14, 2008, 32 pages.
Office Action for U.S. Appl. No. 10/978,722, mail date Sep. 5, 2008, 14 pages.
Amendment and Reply and Terminal Disclaimer for U.S. Appl. No. 10/978,722, mail date Dec. 5, 2008, 29 pages.
Office Action for U.S. Appl. No. 10/978,722, mail date Mar. 4, 2009, 10 pages.
Request for Continued Examination (RCE), Amendment and Reply and Declaration Under 1.131 for U.S. Appl. No. 10/978,722, mail date Jun. 4, 2009, 29 pages.
Notice of Allowance for U.S. Appl. No. 10/978,722, mail date Jul. 9, 2009, 8 pages.
Amendment Under 1.312 and Interview Summary for U.S. Appl. No. 10/978,722, mail date Aug. 7, 2009, 16 pages.
Response to 1.312 Amendment for U.S. Appl. No. 10/978,722, mail date Oct. 8, 2009, 2 pages.
Restriction Requirement for U.S. Appl. No. 10/978,970, mail date Dec. 28, 2007, 8 pages.
Amendment and Reply for U.S. Appl. No. 10/978,970, mail date Jan. 25, 2008, 15 pages.
Office Action for U.S. Appl. No. 10/978,970, mail date Mar. 18, 2008, 18 pages.
Amendment and Reply for U.S. Appl. No. 10/978,970, mail date Jul. 18, 2008, 26 pages.
Office Action for U.S. Appl. No. 10/978,970, mail date Nov. 5, 2008, 17 pages.
Request for Continued Examination (RCE), Amendment and Reply and Declaration Under 1.131 for U.S. Appl. No. 10/978,970, mail date Feb. 5, 2009, 37 pages.
Office Action for U.S. Appl. No. 10/978,970, mail date Mar. 23, 2009, 7 pages.
Amendment and Reply for U.S. Appl. No. 10/978,970, mail date Jun. 12, 2009, 16 pages.
Notice of Allowance for U.S. Appl. No. 10/978,970, mail date Jun. 30, 2009, 8 pages.
Amendment Under 1.312 for U.S. Appl. No. 10/978,970, mail date Sep. 16, 2009, 3 pages.
Response for U.S. Appl. No. 10/978,970, mail date Sep. 30, 2009, 2 pages.

(56) References Cited

OTHER PUBLICATIONS

Office Action for U.S. Appl. No. 12/511,942, mail date Oct. 15, 2009, 12 pages.
Amendment and Reply for U.S. Appl. No. 12/511,942, mail date Jan. 15, 2010, 14 pages.
Office Action for U.S. Appl. No. 12/511,942, mail date Mar. 31, 2010, 4 pages.
Reply and Terminal Disclaimers for U.S. Appl. No. 12/511,942, mail date May 11, 2010, 16 pages.
Notice of Allowance for U.S. Appl. No. 12/511,942, mail date Jun. 2, 2010, 4 pages.
Office Action for U.S. Appl. No. 12/567,415, mail date Oct. 28, 2009, 14 pages.
Amendment and Reply for U.S. Appl. No. 12/567,415, mail date Jan. 27, 2010, 15 pages.
Office Action for U.S. Appl. No. 12/567,415, mail date May 7, 2010, 5 pages.
Reply and Terminal Disclaimers for U.S. Appl. No. 12/567,415, mail date Jul. 6, 2010, 18 pages.
Notice of Allowance for U.S. Appl. No. 12/567,415, mail date Jul. 22, 2010, 4 pages.
Restriction Requirement for U.S. Appl. No. 12/510,857, mail date Oct. 15, 2009, 8 pages.
Amendment and Reply for U.S. Appl. No. 12/510,857, mail date Dec. 9, 2009, 9 pages.
Office Action for U.S. Appl. No. 12/510,857, mail date Feb. 19, 2010, 8 pages.
Amendment and Reply for U.S. Appl. No. 12/510,857, mail date Jun. 21, 2010, 16 pages.
Office Action for U.S. Appl. No. 12/510,857, mail date Aug. 3, 2010, 6 pages.
Reply and Terminal Disclaimer for U.S. Appl. No. 12/510,857, mail date Aug. 30, 2010, 10 pages.
Advisory Action for U.S. Appl. No. 12/510,857, mail date Sep. 3, 2010, 3 pages.
Reply and Terminal Disclaimer for U.S. Appl. No. 12/510,857, mail date Sep. 22, 2010, 7 pages.
Advisory Action for U.S. Appl. No. 12/510,857, mail date Sep. 30, 2010, 2 pages.
Advisory Action for U.S. Appl. No. 12/510,857, mail date Oct. 14, 2010, 3 pages.
Reply for U.S. Appl. No. 12/510,857, mail date Nov. 3, 2010, 6 pages.
Notice of Allowance for U.S. Appl. No. 12/510,857, mail date Nov. 12, 2010, 9 pages.
Office Action for U.S. Appl. No. 10/979,043, mail date Apr. 2, 2008, 14 pages.
Amendment and Reply and Declaration Under 1.131 for U.S. Appl. No. 10/979,043, mail date Aug. 4, 2008, 60 pages.
Office Action for U.S. Appl. No. 10/979,043, mail date Oct. 21, 2008, 9 pages.
Amendment and Reply for U.S. Appl. No. 10/979,043, mail date Jan. 8, 2009, 17 pages.
Office Action for U.S. Appl. No. 10/979,043, mail date Feb. 26, 2009, 9 pages.
Amendment and Reply for U.S. Appl. No. 10/979,043, mail date May 19, 2009, 16 pages.
Office Action for U.S. Appl. No. 10/979,043, mail date Jul. 29, 2009, 10 pages.
Amendment and Reply and Terminal Disclaimer for U.S. Appl. No. 10/979,043, mail date Oct. 26, 2009, 18 pages.
Advisory Action for U.S. Appl. No. 10/979,043, mail date Nov. 4, 2009, 3 pages.
Advisory Action for U.S. Appl. No. 10/979,043, mail date Nov. 12, 2009, 3 pages.
Request for Continued Examination (RCE) and Amendment and Reply for U.S. Appl. No. 10/979,043, mail date Nov. 25, 2009, 15 pages.
Notice of Allowance for U.S. Appl. No. 10/979,043, mail date Dec. 28, 2009, 14 pages.
Amendment Under 1.312 for U.S. Appl. No. 10/979,043, mail date Mar. 5, 2010, 10 pages.
Response to Amendment Under 1.312 for U.S. Appl. No. 10/979,043, mail date Mar. 10, 2010, 2 pages.
Petition for Withdrawal from Issue and Request for Continued Examination (RCE) for U.S. Appl. No. 10/979,043, mail date Jun. 4, 2010, 6 pages.
Notice of Allowance for U.S. Appl. No. 10/979,043, mail date Jun. 16, 2010, 8 pages.
Office Action for U.S. Appl. No. 10/978,681, mail date Mar. 18, 2008, 6 pages.
Amendment and Reply and Terminal Disclaimer for U.S. Appl. No. 10/978,681, mail date May 28, 2008, 19 pages.
Notice of Allowance for U.S. Appl. No. 10/978,681, mail date Jul. 16, 2008, 8 pages.
Request for Continued Examination for U.S. Appl. No. 10/978,681, mail date Oct. 2, 2008, 4 pages.
Notice of Allowance for U.S. Appl. No. 10/978,681, mail date Oct. 24, 2008, 8 pages.
Notice of Withdrawal from Issue for U.S. Appl. No. 10/978,681, mail date Nov. 20, 2008, 1 page.
Office Action for U.S. Appl. No. 10/978,681, mail date Dec. 9, 2008, 13 pages.
Amendment and Reply for U.S. Appl. No. 10/978,681, mail date Mar. 6, 2009, 19 pages.
Office Action for U.S. Appl. No. 10/978,681, mail date May 22, 2009, 7 pages.
Amendment and Reply and Terminal Disclaimer for U.S. Appl. No. 10/978,681, mail date Jul. 20, 2009, 16 pages.
Notice of Allowance for U.S. Appl. No. 10/978,681, mail date Sep. 22, 2009, 7 pages.
Restriction Requirement for U.S. Appl. No. 10/979,041, mail date Jan. 30, 2008, 8 pages.
Reply and Amendment for U.S. Appl. No. 10/979,041, mail date Feb. 22, 2008, 6 pages.
Office Action for U.S. Appl. No. 10/979,041, mail date Apr. 4, 2008, 13 pages.
Reply and Amendment and Declaration Under 1.131 for U.S. Appl. No. 10/979,041, mail date Aug. 4, 2008, 64 pages.
Office Action for U.S. Appl. No. 10/979,041, mail date Oct. 20, 2008, 11 pages.
Amendment and Reply for U.S. Appl. No. 10/979,041, mail date Mar. 6, 2009, 19 pages.
Terminal Disclaimer for U.S. Appl. No. 10/979,041, mail date Apr. 21, 2009, 3 pages.
Notice of Allowance for U.S. Appl. No. 10/979,041, mail date Apr. 30, 2009, 7 pages.
International Search Report and Written Opinion for Application No. PCT/US2008/066801, mail date Oct. 29, 2008, 10 pages.
International Search Report and Written Opinion for Application No. PCT/US2008/066803, mail date Oct. 7, 2008, 12 pages.
International Search Report and Written Opinion for Application No. PCT/US2008/066809, mail date Oct. 29, 2008, 8 pages.
International Search Report and Written Opinion for International Application No. PCT/US2008/082598, mail date Feb. 18, 2009, 11 pages.
International Search Report for PCT/US2005/038761, mail date Oct. 4, 2006, 2 pages.
International Search Report for PCT/US2005/038762, mail date Oct. 2, 2006, 2 pages.
International Search Report for PCT/US2005/038942, mail date Mar. 2, 2006, 3 pages.
International Search Report for PCT/US2005/038943, mail date Mar. 16, 2006, 4 pages.
International Search Report for PCT/US2005/038944, mail date Mar. 31, 2006, 3 pages.
International Search Report for PCT/US2005/038970, mail date Oct. 25, 2006, 3 pages.

\* cited by examiner

LITHIUM-ION BATTERY

CROSS-REFERENCE TO RELATED APPLICATIONS

This application is a continuation-in-part of application Ser. No. 12/510,857, filed Jul. 28, 2009, which issued on Dec. 28, 2010, as U.S. Pat. No. 7,858,236 and is a division of application Ser. No. 10/979,041, filed Oct. 29, 2004, which issued on Sep. 1, 2009 as U.S. Pat. No. 7,582,387, and this application is also a continuation-in-part of application Ser. No. 12/564,818, filed Sep. 22, 2009, which issued on Feb. 8, 2011 as U.S. Pat. No. 7,883,790 and is a division of application Ser. No. 10/978,970, filed Oct. 29, 2004, which issued on Jan. 5, 2010 as U.S. Pat. No. 7,641,992, the entire disclosures of application Ser. Nos. 12/510,857, 10/979,041, 12/564,818, and 10/978,970 are incorporated herein by reference.

BACKGROUND

The present invention relates generally to the field of lithium batteries. Specifically, the present invention relates to lithium-ion batteries that are relatively tolerant to over-discharge conditions and medical devices which utilize such batteries.

Lithium-ion batteries include a positive current collector (e.g., aluminum such as an aluminum foil) having an active material provided thereon (e.g., $LiCoO_2$) and a negative current collector (e.g., copper such as a copper foil) having an active material (e.g., a carbonaceous material such as graphite) provided thereon. Together the positive current collector and the active material provided thereon are referred to as a positive electrode, while the negative current collector and the active material provided thereon are referred to as a negative electrode.

FIG. 1 shows a schematic representation of a portion of a lithium-ion battery 10 such as that described above. The battery 10 includes a positive electrode 20 that includes a positive current collector 22 and a positive active material 24, a negative electrode 30 that includes a negative current collector 32 and a negative active material 34, an electrolyte material 40, and a separator (e.g., a polymeric microporous separator, not shown) provided intermediate or between the positive electrode 20 and the negative electrode 30. The electrodes 20, 30 may be provided as relatively flat or planar plates or may be wrapped or wound in a spiral or other configuration (e.g., an oval configuration). The electrode may also be provided in a folded configuration.

During charging and discharging of the battery 10, lithium ions move between the positive electrode 20 and the negative electrode 30. For example, when the battery 10 is discharged, lithium ions flow from the negative electrode 30 to the to the positive electrode 20. In contrast, when the battery 10 is charged, lithium ions flow from the positive electrode 20 to the negative electrode 30.

FIG. 2 is a graph 100 illustrating the theoretical charging and discharging behavior for a conventional lithium-ion battery. Curve 110 represents the electrode potential versus a lithium reference electrode for a positive electrode that includes an aluminum current collector having a $LiCoO_2$ active material provided thereon, while curve 120 represents the electrode potential versus a lithium reference electrode for a negative electrode that includes a copper current collector having a carbonaceous active material provided thereon. The difference between curves 110 and 120 is representative of the overall cell voltage.

As shown in FIG. 2, upon initial charging to full capacity, the potential of the positive electrode, as shown by curve 110, increases from approximately 3.0 volts to a point above the corrosion potential of copper used to form the negative electrode (designated by dashed line 122). The potential of the negative electrode decreases from approximately 3.0 volts to a point below the decomposition potential of the $LiCoO_2$ active material provided on the aluminum current collector (designated by dashed line 112). Upon initial charging, the battery experiences an irreversible loss of capacity due to the formation of a passive layer on the negative current collector, which may be referred to as a solid-electrolyte interface ("SEI"). The irreversible loss of capacity is shown as a ledge or shelf 124 in curve 120.

One difficulty with conventional lithium-ion batteries is that when such a battery is discharged to a point near zero volts, it may exhibit a loss of deliverable capacity and corrosion of the negative electrode current collector (copper) and possibly of the battery case, depending on the material used and the polarity of the case. As shown in FIG. 2, after initial charging of the battery, a subsequent discharge of the battery in which the voltage of the battery approaches zero volts (i.e., zero percent capacity) results in a negative electrode potential that follows a path designated by dashed line 126. As shown in FIG. 2, the negative electrode potential levels off or plateaus at the copper corrosion potential of the negative current collector (approximately 3.5 volts for copper and designated by dashed line 122 in FIG. 2).

The point at which the curves 110 and 120 cross is sometimes referred to as the zero voltage crossing potential, and corresponds to a cell voltage that is equal to zero (i.e., the difference between the two curves equals zero at this point). Because of the degradation of the copper current collector which occurs at the copper corrosion potential, the copper material used for the negative current collector corrodes before the cell reaches a zero voltage condition, resulting in a battery that exhibits a dramatic loss of deliverable capacity.

While FIG. 2 shows the theoretical charging and discharging behavior of a battery that may experience corrosion of the negative current collector when the battery approaches a zero voltage configuration, it should be noted that there may also be cases in which the active material on the positive current collector may degrade in near-zero-voltage conditions. In such cases, the theoretical charging and discharging potential of the positive electrode versus a lithium reference electrode would decrease to the decomposition potential of the positive active material (shown as line 112 in FIG. 2), at which point the positive active material would decompose, resulting in potentially decreased protection against future over-discharge conditions.

Because damage to the lithium-ion battery may occur in the event of a low voltage condition, conventional lithium-ion batteries may include protection circuitry and/or may be utilized in devices that include protection circuitry which substantially reduces the current drain from the battery (e.g., by disconnecting the battery).

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life.

It may be desirable to provide a source of battery power for such medical devices, including implantable medical devices. In such cases, it may be advantageous to provide a battery that may be recharged. It may also be advantageous to provide a battery that may be discharged to a near zero voltage condition without substantial risk that the battery may be damaged (e.g., without corroding one of the electrodes or the battery case, decomposing the positive active material, etc.) such that the performance of the battery is degraded in subsequent charging and discharging operations.

It would be advantageous to provide a battery (e.g., a lithium-ion battery) that may be discharged to near zero volts without producing a subsequent decrease in the amount of deliverable capacity or producing a corroded negative electrode or battery case. It would also be advantageous to provide a battery that compensates for the irreversible loss of capacity resulting from initial charging of the battery to allow the battery to be used in near zero voltage conditions without significant degradation to battery performance. It would also be advantageous to provide a medical device (e.g., an implantable medical device) that utilizes a battery that includes any one or more of these or other advantageous features.

SUMMARY

An exemplary embodiment relates to a lithium-ion battery that includes a positive electrode that includes a positive current collector, a first active material, and a second active material. The lithium-ion battery also includes a negative electrode comprising a negative current collector, a third active material, and a quantity of lithium in electrical contact with the negative current collector. The first active material, second active material, and third active materials are configured to allow doping and undoping of lithium ions, and the second active material exhibits charging and discharging capacity below a corrosion potential of the negative current collector and above a decomposition potential of the first active material.

Another exemplary embodiment relates to a lithium-ion battery that includes a positive electrode comprising a current collector having a primary active material and a secondary active material provided on at least one side thereof. The lithium-ion battery also includes a negative electrode having a negative current collector and an active material provided on the negative current collector. The secondary active material does not include lithium and provides charging and discharging capacity for the positive electrode below a corrosion potential of the negative current collector and above a decomposition potential of the primary active material.

Another exemplary embodiment relates to a lithium-ion battery that includes a positive electrode comprising a current collector having a primary active material and a secondary active material provided on at least one side thereof. The lithium-ion battery also includes a negative electrode having a negative current collector and an active material provided on the negative current collector. A quantity of lithium is in electrical contact with the negative current collector. The secondary active material does not include lithium and provides charging and discharging capacity for the positive electrode below a corrosion potential of the negative current collector and above a decomposition potential of the primary active material.

Another embodiment relates to a medical device that includes a rechargeable lithium-ion battery for providing power to the medical device. The lithium-ion battery includes a positive electrode including a current collector and a first active material, a negative electrode including a current collector and a second active material, and an auxiliary electrode including a current collector and a third active material. The auxiliary electrode is configured for selective electrical connection to one of the positive electrode and the negative electrode. The first active material, second active material, and third active material are configured to allow doping and undoping of lithium ions. The third active material exhibits charging and discharging capacity below a corrosion potential of the current collector of the negative electrode and above a decomposition potential of the first active material.

Another exemplary embodiment relates to a device for providing a therapeutic treatment to a patient. The device includes a rechargeable battery for providing power for the device. The battery includes a first electrode including a first current collector and a first active material provided on the first current collector; a second electrode including a second current collector and a second active material provided on the second current collector; and a third electrode including a third current collector and a third active material provided on the third current collector. The third electrode is configured for selective electrical coupling to and decoupling from the second electrode.

Another exemplary embodiment relates to a system for providing a medical treatment to a patient. The system includes a lithium-ion battery configured to provide power to the system and capable of being charged and discharged. The lithium-ion battery includes a positive electrode having a positive current collector and an active material provided on at least one side of the positive current collector. The lithium-ion battery also includes a negative electrode having a negative current collector and a primary active material provided on at least one side of the negative current collector. The lithium-ion battery also includes an auxiliary electrode having a current collector and an auxiliary active material provided on at least one side of the current collector of the auxiliary electrode. The auxiliary electrode configured to be selectively coupled to the negative electrode when a predetermined condition is present.

Another exemplary embodiment relates to a method of treating a medical condition of a patient that includes providing at least a portion of a medical device in contact with the patient and providing a treatment to the patient utilizing the medical device. The medical device receives power from a battery that includes a positive electrode having a current collector and a first active material, a negative electrode having a current collector and a second active material, and an auxiliary electrode having a current collector and a third active material. The auxiliary electrode is configured for selective electrical connection to one of the positive electrode and the negative electrode. The first active material, second active material, and third active material are configured to allow doping and undoping of lithium ions, and the third active material exhibits charging and discharging capacity below a corrosion potential of the current collector of the negative electrode and above a decomposition potential of the first active material.

DETAILED DESCRIPTION OF THE EXEMPLARY EMBODIMENTS

Figure 1:
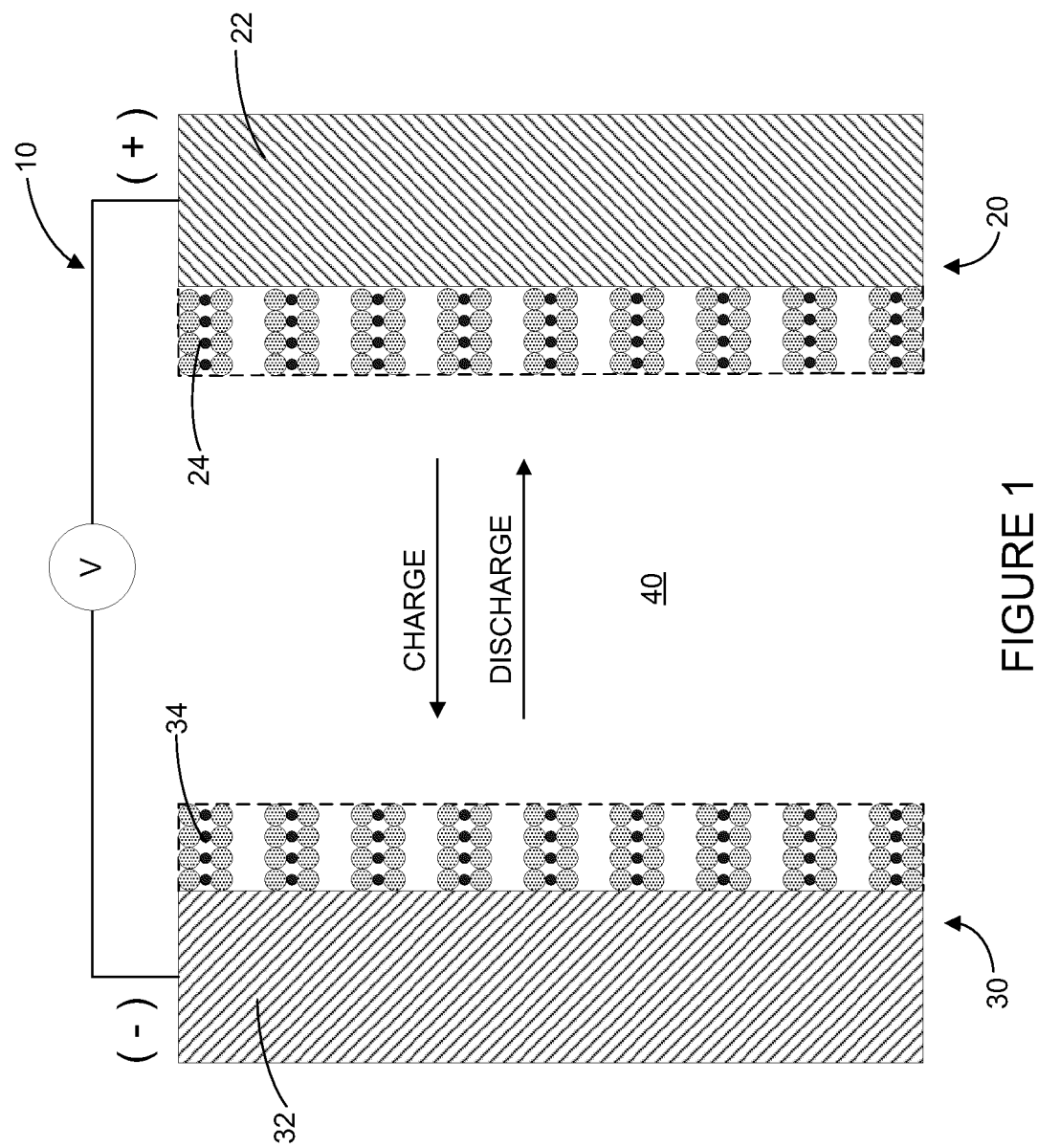
FIG. 1 is a schematic cross-sectional view of a conventional lithium-ion battery.
Figure 2:
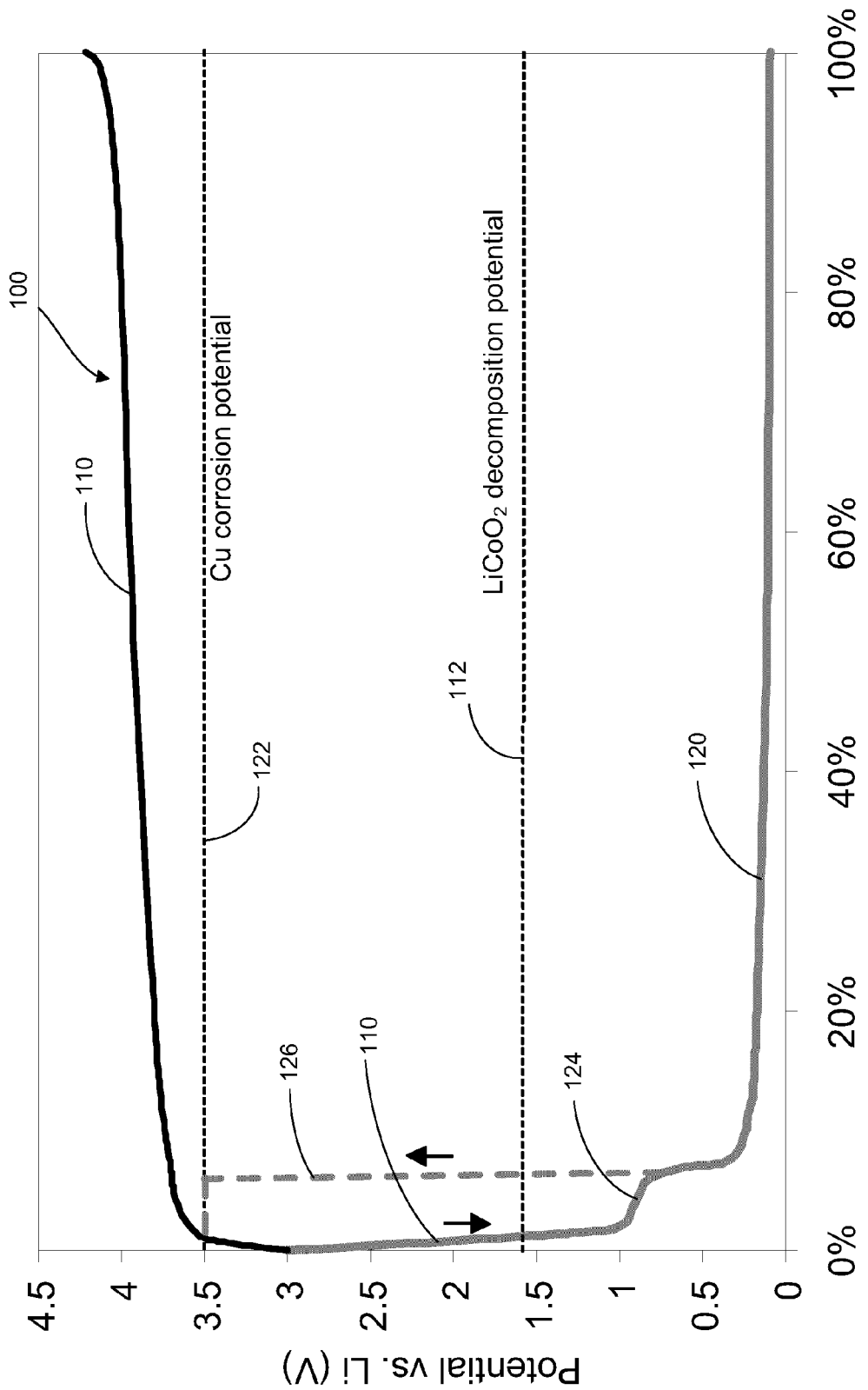
FIG. 2 is a graph illustrating the theoretical charging and discharging behavior for a conventional lithium-ion battery such as that shown schematically in FIG. 1.
Figure 3:
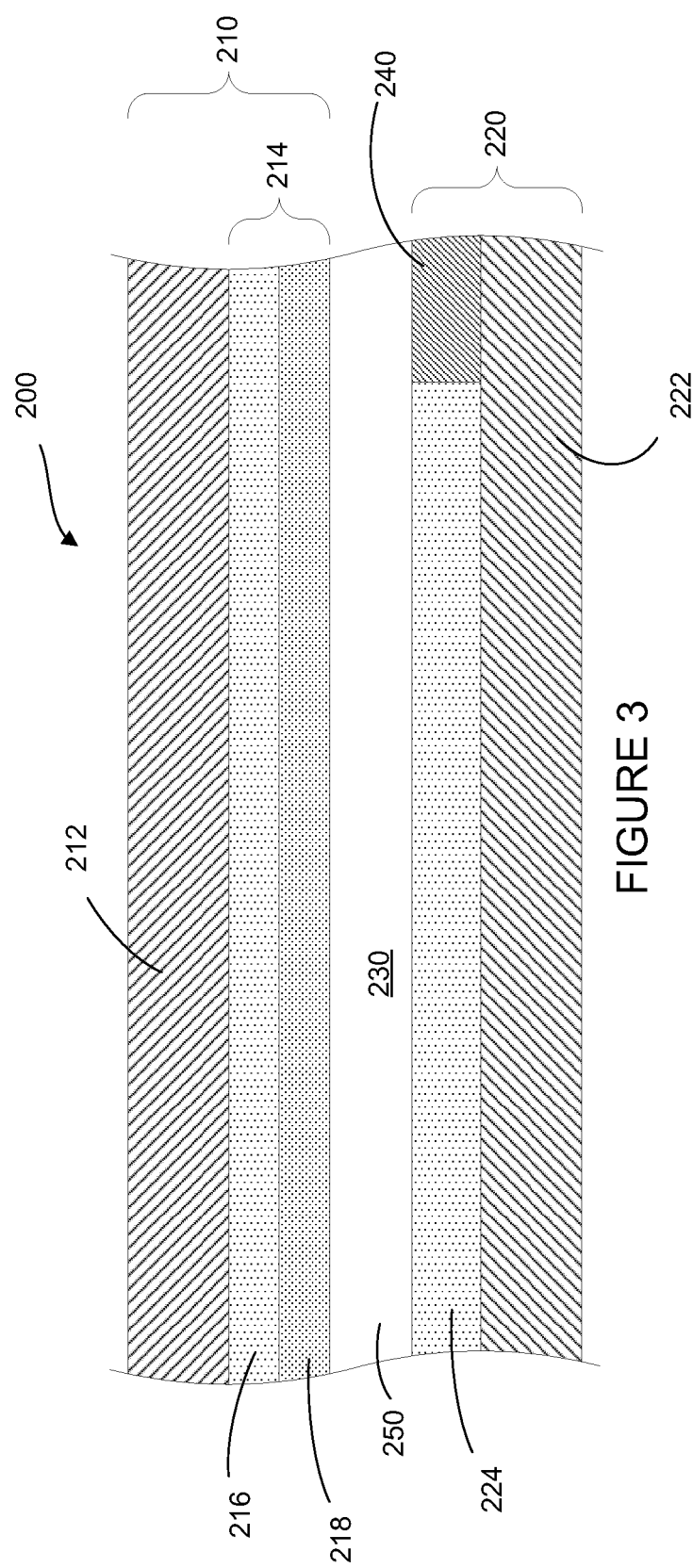
FIG. 3 is a schematic cross-sectional view of a portion of a lithium-ion battery according to an exemplary embodiment.

With reference to FIG. 3, a schematic cross-sectional view of a portion of a lithium-ion battery 200 is shown according to an exemplary embodiment. According to an exemplary embodiment, the battery 200 has a rating of between approximately 10 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery.

The battery 200 includes at least one positive electrode 210 and at least one negative electrode 220. The electrodes may be provided as flat or planar components of the battery 200, may be wound in a spiral or other configuration, or may be provided in a folded configuration. For example, the electrodes may be wrapped around a relatively rectangular mandrel such that they form an oval wound coil for insertion into a relatively prismatic battery case. According to other exemplary embodiments, the battery may be provided as a button cell battery, a thin film solid state battery, or as another lithium-ion battery configuration.

The battery case (not shown) may be made of stainless steel or another metal. According to an exemplary embodiment, the battery case may be made of titanium, aluminum, or alloys thereof. According to another exemplary embodiment, the battery case may be made of a plastic material or a plastic-foil laminate material (e.g., an aluminum foil provided intermediate a polyolefin layer and a polyester layer).

According to an exemplary embodiment, the negative electrode is coupled to a stainless steel case by a member or tab comprising nickel or a nickel alloy. An aluminum or aluminum alloy member or tab may be coupled or attached to the positive electrode. The nickel and aluminum tabs may serve as terminals for the battery according to an exemplary embodiment.

The dimensions of the battery 200 may differ according to a variety of exemplary embodiments. For example, according to one exemplary embodiment in which the electrodes are wound such that they may be provided in a relatively prismatic battery case, the battery has dimensions of between approximately 30-40 mm by between approximately 20-30 mm by between approximately 5-7 mm. According to another exemplary embodiment, the dimensions of the battery are approximately 20 mm by 20 mm by 3 mm. According to another exemplary embodiment, a battery may be provided in the form of a button cell type battery having a diameter of approximately 30 mm and a thickness of approximately 3 mm. It will be appreciated by those of skill in the art that such dimensions and configurations as are described herein are illustrative only, and that batteries in a wide variety of sizes, shapes, and configurations may be produced in accordance with the novel concepts described herein.

An electrolyte 230 is provided intermediate or between the positive and negative electrodes to provide a medium through which lithium ions may travel. According to an exemplary embodiment, the electrolyte may be a liquid (e.g., a lithium salt dissolved in one or more non-aqueous solvents). According to another exemplary embodiment, the electrolyte may be a lithium salt dissolved in a polymeric material such as poly (ethylene oxide) or silicone. According to another exemplary embodiment, the electrolyte may be an ionic liquid such as N-methyl-N-alkylpyrrolidinium bis(trifluoromethanesulfonyl)imide salts. According to another exemplary embodiment, the electrolyte may be a solid state electrolyte such as a lithium-ion conducting glass such as lithium phosphorous oxynitride (LiPON).

Various other electrolytes may be used according to other exemplary embodiments. For example, according to an exemplary embodiment, the electrolyte may be a 1:1 mixture of ethylene carbonate to diethylene carbonate (EC:DEC) in a 1.0 M salt of $LiPF_6$. According to another exemplary embodiment, the electrolyte may include a polypropylene carbonate solvent and a lithium bis-oxalatoborate salt (sometimes referred to as LiBOB). According to other exemplary embodiments, the electrolyte may comprise one or more of a PVDF copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, lithium conducting ceramics, and an inorganic ionic liquid or gel, among others.

A separator 250 is provided intermediate or between the positive electrode 210 and the negative electrode 220. According to an exemplary embodiment, the separator 250 is a polymeric material such as a polypropylene/polyethelene copolymer or another polyolefin multilayer laminate that includes micropores formed therein to allow electrolyte and lithium ions to flow from one side of the separator to the other. The thickness of the separator 250 is between approximately 10 micrometers (μm) and 50 μm according to an exemplary embodiment. According to a particular exemplary embodiment, the thickness of the separator is approximately 25 μm and the average pore size of the separator is between approximately 0.02 μm and 0.1 μm.

The positive electrode 210 includes a current collector 212 made of a conductive material such as a metal. According to an exemplary embodiment, the current collector 212 comprises aluminum or an aluminum alloy. According to an exemplary embodiment, the thickness of the current collector 212 is between approximately 5 μm and 75 μm. According to a particular exemplary embodiment, the thickness of the current collector 212 is approximately 20 μm. It should also be noted that while the positive current collector 212 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 212 has a layer of active material 214 provided thereon (e.g., coated on the current collector). While FIG. 3 shows that the layer of active material 214 is provided on only one side of the current collector 212, it should be understood that a layer of active material similar or identical to that shown as layer 214 may be provided or coated on both sides of the current collector 212.

Figure 4:
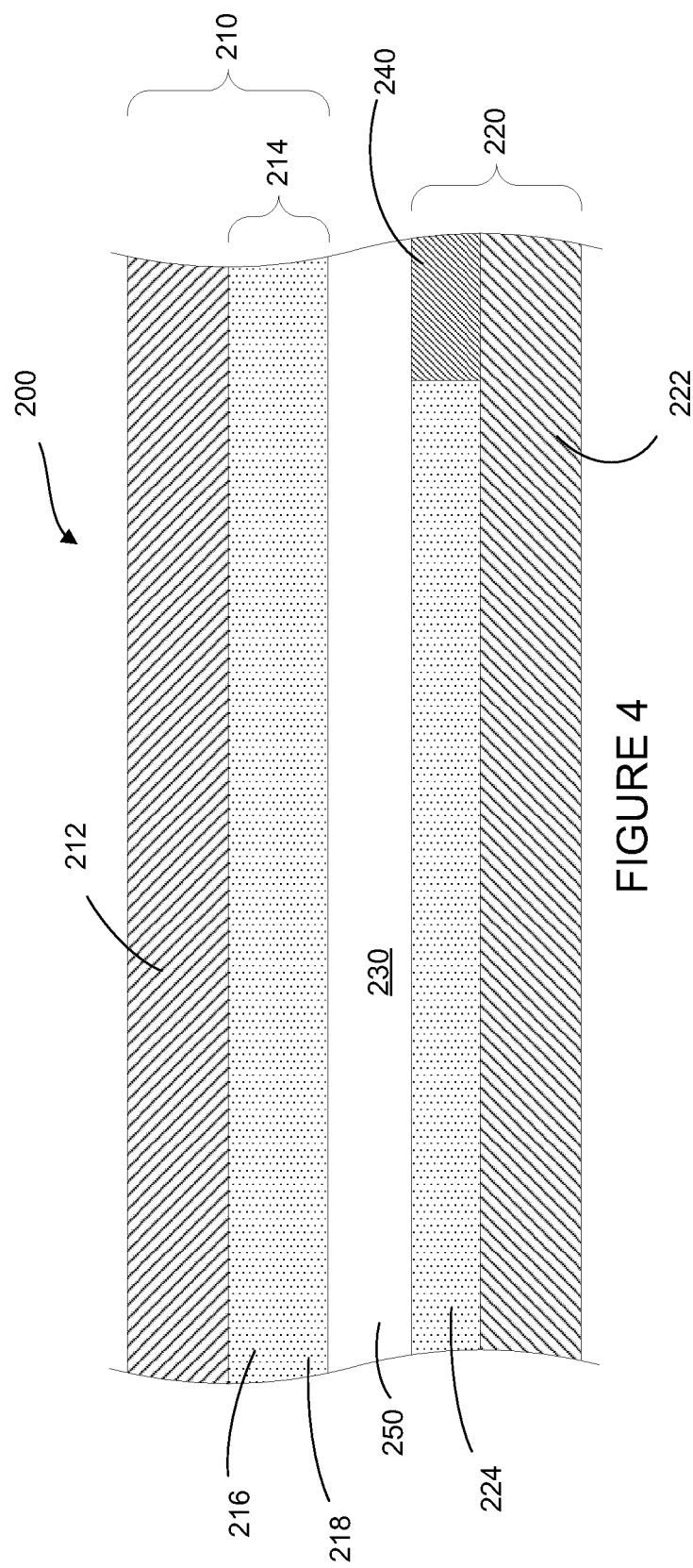
FIG. 4 is a schematic cross-sectional view of a portion of a lithium-ion battery according to another exemplary embodiment.

As shown in FIG. 3, layer 214 includes a primary active material 216 and a secondary or auxiliary active material 218. While the primary active material 216 and the secondary active material 218 are shown as being provided as separate individual layers according to an exemplary embodiment, it will be appreciated that the primary active material 216 and the secondary active material 218 may be provided as a single active material layer in which the primary and secondary active materials are intermixed (see, e.g., the exemplary embodiment shown in FIG. 4, in which layer 214 includes both the primary active material 216 and the secondary active material 218). A binder material may also be utilized in conjunction with the layer of active material 214 to bond or hold the various electrode components together. For example, according to an exemplary embodiment, the layer of active material may include a conductive additive such as carbon black and a binder such as polyvinylidine fluoride (PVDF) or an elastomeric polymer.

According to an exemplary embodiment, the primary active material 216 is a material or compound that includes lithium. The lithium included in the primary active material 216 may be doped and undoped during discharging and charging of the battery, respectively. According to an exemplary embodiment, the primary active material 216 is lithium cobalt oxide ($LiCoO_2$). According to another exemplary embodiment, the positive active material is of the form $LiCo_xNi_{(1-x)}O_2$, where x is between approximately 0.05 and 0.8. According to another exemplary embodiment, the primary active material is of the form $LiAl_xCo_yNi_{(1-x-y)}O_2$, where x is between approximately 0.05 and 0.3 and y is between approximately 0.1 and 0.3. According to other exemplary embodiments, the primary active material may include $LiMn_2O_4$.

According to various other exemplary embodiments, the primary active material may include a material such as a material of the form $Li_{1-x}MO_2$ where M is a metal (e.g., $LiCoO_2$, $LiNiO_2$, and $LiMnO_2$), a material of the form $Li_{1-w}(M'_xM''_y)O_2$ where M' and M'' are different metals (e.g., $Li(Ni_xMn_y)O_2$, $Li(Ni_{1/2}Mn_{1/2})O_2$, $Li(Cr_xMn_{1-x})O_2$, $Li(Al_xMn_{1-x})O_2$, $Li(Co_xM_{1-x})O_2$ where M is a metal, $Li(Co_xNi_{1-x})O_2$, and $Li(Co_xFe_{1-x})O_2$)), a material of the form $Li_{1-w}(Mn_xNi_yCo_z)O_2$ (e.g., $LiCo_xMn_yNi_{(1-x-y)}O_2$, $Li(Mn_{1/3}Ni_{1/3}Co_{1/3})O_2$, $Li(Mn_{1/3}Ni_{1/3}Co_{1/3-x}Mg_x)O_2$, $Li(Mn_{0.4}Ni_{0.4}Co_{0.2})O_2$, and $Li(Mn_{0.1}Ni_{0.1}Co_{0.8})O_2$), a material of the form $Li_{1-w}(Mn_xNi_xCo_{1-2x})O_2$, a material of the form $Li_{1-w}(Mn_xNi_yCo_zAl_w)O_2$, a material of the form $Li_{1-w}(Ni_xCo_yAl_z)O_2$ (e.g., $Li(Ni_{0.8}Co_{0.15}Al_{0.05})O_2$), a material of the form $Li_{1-w}(Ni_xCo_yM_z)O_2$ where M is a metal, a material of the form $Li_{1-w}(Ni_xMn_yM_z)O_2$ where M is a metal, a material of the form $Li(Ni_{x-y}Mn_yCr_{2-x})O_4$, $LiMn_2O_4$, a material of the form $LiM'M''_2O_4$ where M' and M'' are different metals (e.g., $LiMn_{2-y-z}Ni_y$, $Li_zO_4$, $LiMn_{1.5}Ni_{0.5}O_4$, $LiNiCuO_4$, $LiMn_{1-x}Al_xO_4$, $LiNi_{0.5}Ti_{0.5}O_4$, and $Li_{1.05}Al_{0.1}Mn_{1.85}O_{4-z}F_z$), $Li_2MnO_3$, a material of the form $Li_xV_yO_z$ (e.g., $LiV_3O_8$, $LiV_2O_5$, and $LiV_6O_{13}$), a material of the form $LiMPO_4$ where M is a metal or $LiM_xM''_{1-x}PO_4$ where M' and M'' are different metals (e.g., $LiFePO_4$, $LiFe_xM_{1-x}PO_4$ where M is a metal, $LiVOPO_4$, and $Li_3V_2(PO_4)_3$, $LiMPO_{4x}$ where M is a metal such as iron or vanadium and X is a halogen such as fluorine, and combinations thereof.

The secondary active material 218 is a material that is selected to have relatively significant cyclable charge and discharge capacity (i.e., cyclable capacity) below the corrosion potential of the material used for a negative current collector 222 provided as part of the negative electrode 220 (and/or any other material to which the negative current collector is electrically attached or in electrical communication with, for example, a case or housing for the battery) and above the decomposition potential of the primary active material 216. For example, according to an exemplary embodiment in which the negative current collector 222 comprises copper, for which the corrosion potential is approximately 3.5 volts, the secondary active material 218 includes significant charge and discharge capacity below 3.5 volts.

The secondary active material 218 may or may not contain lithium. According to an exemplary embodiment in which the secondary active material does not include lithium, the secondary active material is $V_6O_{13}$. According to another exemplary embodiment in which the secondary active material includes lithium, the secondary active material is $LiMn_2O_4$. According to various other exemplary embodiments, the secondary active material may be selected from the following materials and combinations thereof: $V_2O_5$, $V_6O_{13}$, $LiMn_2O_4$ (spinel), $LiM_xMn_{(2-x)}O_4$ (spinel) where M is metal (including Li) and where x is between approximately 0.05 and 0.4, $Li_4Ti_5O_{12}$, $Li_xVO_2$ (where x is between approximately 0 and 1), $V_3O_8$, $MoO_3$, $TiS_2$, $WO_2$, $MoO_2$, and $RuO_2$.

According to an exemplary embodiment, electrochemically active or cyclable lithium may be added as finely divided or powdered lithium. Such powdered lithium may include a passive coating (e.g., a thin layer or film of lithium carbonate) provided thereon to reduce the reactivity of the powdered lithium with air and moisture. Such material may be mixed with the secondary active material prior to application of the secondary active material to fabrication of the cells or may be added as another separate active material layer.

The lithium added to the secondary active material 218 of the positive electrode 210 has significant charge/discharge capacity that lies below the corrosion potential of the negative current collector and/or any battery components to which it is electrically connected (e.g., the case) and above the decomposition potential of the positive electrode active material. The lithium becomes significantly doped at a potential below the corrosion potential for the negative current collector 222. In so doing, this material lowers the final potential of the positive electrode in the discharge state, so that the zero voltage crossing potential remains below the corrosion potential of the negative current collector and the battery case. The secondary active material may be capable of releasing the lithium when the battery is charged.

It should be noted that while a variety of materials have been described above as being useful for secondary active material 218, a variety of additional materials may be utilized in addition to or in place of such materials. For example, the secondary active material may comprise an oxide material such as one or more of $Li_xMoO_3$ ($0<x\le2$), $Li_xMoO_2$ ($0<x\le1$), $Li_xMo_2O_4$ ($0<x\le2$), $Li_xMnO_2$ ($0<x\le1$), $Li_xMn_2O_4$ ($0<x\le2$), $Li_xV_2O_5$ ($0<x\le2.5$), $Li_xV_3O_8$ ($0<x\le3.5$), $Li_xV_6O_{13}$ ($0<x\le6$ for $Li_xVO_{2.19}$ and $0<x\le3.6$ for $Li_xVO_{2.17}$), $Li_xVO_2$ ($0<x\le1$), $Li_xWO_3$ ($0<x\le1$), $Li_xWO_2$ ($0<x\le1$), $Li_xTiO_2$ (anatase) ($0<x\le1$), $Li_xTi_2O_4$ ($0<x\le2$), $Li_xRuO_2$ ($0<x\le1$), $Li_xFe_2O_3$ ($0<x\le2$), $Li_xFe_3O_4$ ($0<x\le2$), $Li_xCr_2O$ ($0<x\le3$), $Li_xCr$ ($0<x\le3.8$), and $Li_xNi_yCo_{1-y}O_2$ ($0<x\le1$, $0.9\le y\le1.00$), where x is selected such that these materials have little or no lithium that becomes undoped below the corrosion potential of the negative current collector during the first charge of the battery.

According to another exemplary embodiment, the secondary active material may comprise a sulfide material such as one or more of $Li_xV_2S_5$ ($0<x\le4.8$), $Li_xTaS_2$ ($0<x\le1$), $Li_xFeS$ ($0<x\le1$), $Li_xFeS_2$ ($0<x\le1$), $Li_xNbS_3$ ($0<x\le2.4$), $Li_xMoS_3$ ($0<x\le3$), $Li_xMoS_2$ ($0<x\le1$), $Li_xTiS_2$ ($0<x\le1$), $Li_xZrS_2$ ($0<x\le1$), $Li_xFe_{0.25}V_{0.75}S_2$ ($0<x\le1$), $Li_xCr_{0.75}V_{0.25}S_2$ ($0<x\le0.65$), and $Li_xCr_{0.5}V_{0.5}S_2$ ($0<x\le1$), where x is selected such that these materials have little or no lithium that becomes undoped below corrosion potential of the negative current collector during the first charge of the battery.

According to another exemplary embodiment, the secondary active material may comprise a selenide material such as one or more of $Li_xNbSe_3$ ($0<x\le3$), $Li_xVSe_2$ ($0<x\le1$). Various other materials may also be used, for example, $Li_xNiPS_3$ ($0<x\le1.5$) and $Li_xFePS_3$ ($0<x\le1.5$), where x is selected such that these materials have little or no lithium that becomes undoped below corrosion potential of the negative current collector during the first charge of the battery.

According to an exemplary embodiment, the thickness of the layer of active material 214 is between approximately 0.1 μm and 3 mm. According to another exemplary embodiment, the thickness of the layer of active material 214 is between approximately 25 μm and 300 μm. According to a particular exemplary embodiment, the thickness of the layer of active material 214 is approximately 75 μm. In embodiments in which the primary active material 216 and the secondary active material 218 are provided as separate layers of active material, the thickness of the primary active material 216 is between approximately 25 μm and 300 μm (and approximately 75 μm according to a particular exemplary embodiment), while the thickness of the secondary active material 218 is between approximately 5 μm and 60 μm (and approximately 10 μm according to a particular exemplary embodiment). The amount of the secondary active material 218 to be added is determined by the electrochemical equivalents (i.e., capacity) of lithium that can be cycled from that material. According to an exemplary embodiment, the amount is as small as practical, because this minimizes the amount to which the battery's average operating voltage (and therefore energy density) is reduced. According to another exemplary embodiment, the amount is at a minimum equal to the difference between the irreversible capacity of the negative electrode active material and that of the positive active material.

The negative current collector 222 included as part of the negative electrode 220 is made of a conductive material such as a metal. According to an exemplary embodiment, the current collector 222 is copper or a copper alloy. According to another exemplary embodiment, the current collector 222 is titanium or a titanium alloy. According to another exemplary embodiment, the current collector 222 is nickel or a nickel alloy. According to another exemplary embodiment in which the negative active material 224 is not carbon, the current collector 222 is aluminum or an aluminum alloy. It should also be noted that while the negative current collector 222 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

According to an exemplary embodiment, the thickness of the current collector 222 is between approximately 100 nm and 100 μm. According to another exemplary embodiment, the thickness of the current collector 222 is between approximately 5 μm and 25 μm. According to a particular exemplary embodiment, the thickness of the current collector 222 is approximately 10 μm.

The negative current collector 222 has a negative active material 224 provided thereon. While FIG. 3 shows that the active material 224 is provided on only one side of the current collector 222, it should be understood that a layer of active material similar or identical to that shown may be provided or coated on both sides of the current collector 222.

According to exemplary embodiment, the negative active material 224 is a carbonaceous material (e.g., carbon such as graphite). According to exemplary embodiment, the negative active material 224 is a lithium titanate material such as $Li_4Ti_5O_{12}$. Other lithium titanate materials which may be suitable for use as the negative active material may include one or more of include the following lithium titanate spinel materials: $H_xLi_{y-x}TiO_xO_4$, $H_xLi_{y-x}TiO_xO_4$, $Li_4M_xTi_{5-x}O_{12}$, $Li_xTi_yO_4$, $Li_xTi_yO_4$, $Li_4[Ti_{1.67}Li_{0.33-y}M_y]O_4$, $Li_2TiO_3$, $Li_4Ti_{4.75}V_{0.25}O_{12}$, $Li_4Ti_{4.75}Fe_{0.25}O_{11.88}$, and $Li_4Ti_{4.5}Mn_{0.5}O_{12}$, and $LiM'M''XO_4$ (where M' is a metal such as nickel, cobalt, iron, manganese, vanadium, copper, chromium, molybdenum, niobium, or combinations thereof, M'' is an optional three valent non-transition metal, and X is zirconium, titanium, or a combination of these two). Note that such lithium titanate spinel materials may be used in any state of lithiation (e.g., $Li_{4+x}Ti_5O_{12}$, where $0\le x\le 3$).

One advantage of using a lithium titanate material instead of a carbonaceous material is that it is believed that the use of a lithium titanate material allows for charging and discharging of the battery at higher rates than is capable using carbonaceous materials. Lithium titanate materials are also believed to offer superior cycle life because they are so called "zero-strain" materials. Zero strain materials have crystal lattices which do not experience shrinkage or contraction with lithium doping/de-doping, making them free from strain-related degradation mechanisms. According to other exemplary embodiments, the negative active material 224 may be carbon, $Li_xAl$, $Li_xSn$, $Li_xSi$, $Li_xSnO$, metal nanoparticle composites (e.g., including $Li_xAl$, $Li_xSn$, $Li_xSi$, or $Li_xSnO$), or carbon-coated lithium titanate.

Another advantageous feature of using a lithium titanate material is that it is believed that when used in a negative electrode of a lithium-ion battery, such materials will cycle lithium at a potential plateau of about 1.5 V versus a lithium reference electrode. This is substantially higher than graphitic carbon, which is traditionally used in lithium ion batteries, and cycles lithium down to about 0.1 V in the fully charged state. As a result, the battery using lithium titanate is believed to be less likely to result in plating of lithium (which occurs at 0 V versus a lithium reference) while being charged. Lithium plating is a well-known phenomenon that can lead to loss in performance of lithium ion batteries. Being free from the risk of lithium plating, cells with lithium titanate negative electrodes may also be charged at rates that exceed those with carbon negative electrodes. For example, a common upper limit for the rate of charge in lithium ion batteries is about 1 C (meaning that the battery can be fully charged from the discharged state in one hour). Conversely, it has been reported in literature that lithium titanate may be charged at rates up to 10 C (i.e., attaining full charge in 1/10 hour, or six minutes). Being able to recharge a battery more quickly substantially increases the functionality of devices that employ such a battery. A further advantage of the higher potential of the lithium titanate material is that it avoids decomposition of organic solvents (such as propylene carbonate) commonly used in lithium ion batteries. In so doing, it may reduce negative consequences such as formation of gas, cell swelling, reduction of reversible battery capacity, and buildup of resistive films which reduce battery power.

A binder material may also be utilized in conjunction with the layer of active material 224. For example, according to an exemplary embodiment, the layer of active material may include a conductive additive such as carbon black and a binder such as polyvinylidine fluoride (PVDF) or an elastomeric polymer.

According to various exemplary embodiments, the thickness of the active material 224 is between approximately 0.1 μm and 3 mm. According to other exemplary embodiments, the thickness of the active material 224 may be between approximately 25 μm and 300 μm. According to another exemplary embodiment, the thickness of the active material 224 may be between approximately 20 μm and 90 μm, and according to a particular exemplary embodiment, may be approximately 75 μm.

As shown in FIG. 3, a mass or quantity of electrochemically active lithium (shown as a piece of lithium in the form of a lithium patch or member 240) is shown as being coupled or attached to (e.g., in electrical contact with) the negative current collector 222. Such a configuration corresponds to a situation in which the secondary active material 228 is provided without including electrochemically active lithium (e.g., the secondary active material 228 does not include lithium as it is coated on the positive current collector). One such exemplary embodiment involves the use of $V_6O_{13}$ for the secondary active material. It should also be noted that electrochemically cyclable lithium may be added by adding lithium-containing compounds such as a lithium intermetallic compound such as a lithium-aluminum compound, a lithium-tin compound, a lithium-silicon compound, or any other similar compound that irreversibly donates lithium at a potential below that of the corrosion potential of the negative current collector (and any material to which it is electrically connected).

The electrochemically active lithium may be provided in other locations in the negative electrode 220 and/or may have a different size or shape than that shown schematically in FIG. 3. For example, the electrochemically active lithium may be provided as a disc or as a rectangular piece of material coupled to the negative current collector. While the electrochemically active lithium is shown as being provided on a single side of the current collector 222 in FIG. 3 (e.g., as a lithium patch), separate lithium patches may be provided on opposite sides of the current collector 222. Further, multiple lithium patches may be provided on one or more of the sides of the current collector 222. In another example, the lithium may be provided elsewhere within the battery and connected (e.g., by a wire) to the current collector 222.

According to another exemplary embodiment, the electrochemically active or cyclable lithium may be added as finely divided or powdered lithium. Such powdered lithium may include a passive coating (e.g., a thin layer or film of lithium carbonate) provided thereon to reduce the reactivity of the powdered lithium with air and moisture. Such material may be mixed with the negative electrode active material prior to application of the negative electrode active material to fabrication of the cells or may be added as another separate active material layer. According to an exemplary embodiment, the finely divided or powdered lithium particles have a diameter of between approximately 1 μm and 100 μm, and according to a particular embodiment, between approximately 5 μm and 30 μm.

One advantage of providing electrochemically active lithium at the negative electrode (e.g., in the form of one or more lithium patches) is that the secondary active material 228 may be partially or completely lithiated by the lithium to compensate for the irreversible loss of capacity which occurs upon the first charging of the battery 200. For example, when the battery cell is filled with electrolyte, lithium from the lithium patch 240 is oxidized and inserted into the negative active material (i.e., the lithium in the electrochemically active lithium is effectively "shorted" to the negative active material).

The electrochemically active lithium may also provide a number of additional advantages. For example, it may act to maintain the potential of the negative current collector below its corrosion potential prior to initial charging ("formation") of the battery. The electrochemically active lithium may also aid in the formation of the solid-electrolyte interface ("SEI") at the negative electrode. Further, the electrochemically active lithium may provide the "formation" of the active material on the negative electrode without a corresponding reduction in battery capacity as would occur when the source of lithium for formation is the active material from the positive electrode.

The amount of electrochemically active lithium is selected such the amount of electrochemical equivalents provided by the electrochemically active lithium at minimum corresponds to the irreversible capacity of the negative electrode active material and at maximum corresponds to the sum of the irreversible capacity of the negative electrode active material and the capacity of the secondary active material 228. In this manner, the electrochemically active lithium at least compensates for the irreversible loss of capacity which occurs on initial charging of the battery 200 and most preferably corresponds to the sum of the irreversible capacity of the negative electrode active material and the capacity of the secondary active material 228.

According to an exemplary embodiment in which a lithium patch 240 is utilized, the size the lithium patch 240 is between approximately 1.4 cm×1.4 cm×0.11 cm, which corresponds to approximately 0.013 grams (e.g., approximately 50 mAh). The specific size of the lithium patch may vary according to other exemplary embodiments (e.g., approximately 5-25 percent of the capacity of either the negative or positive electrode).

Figure 5:
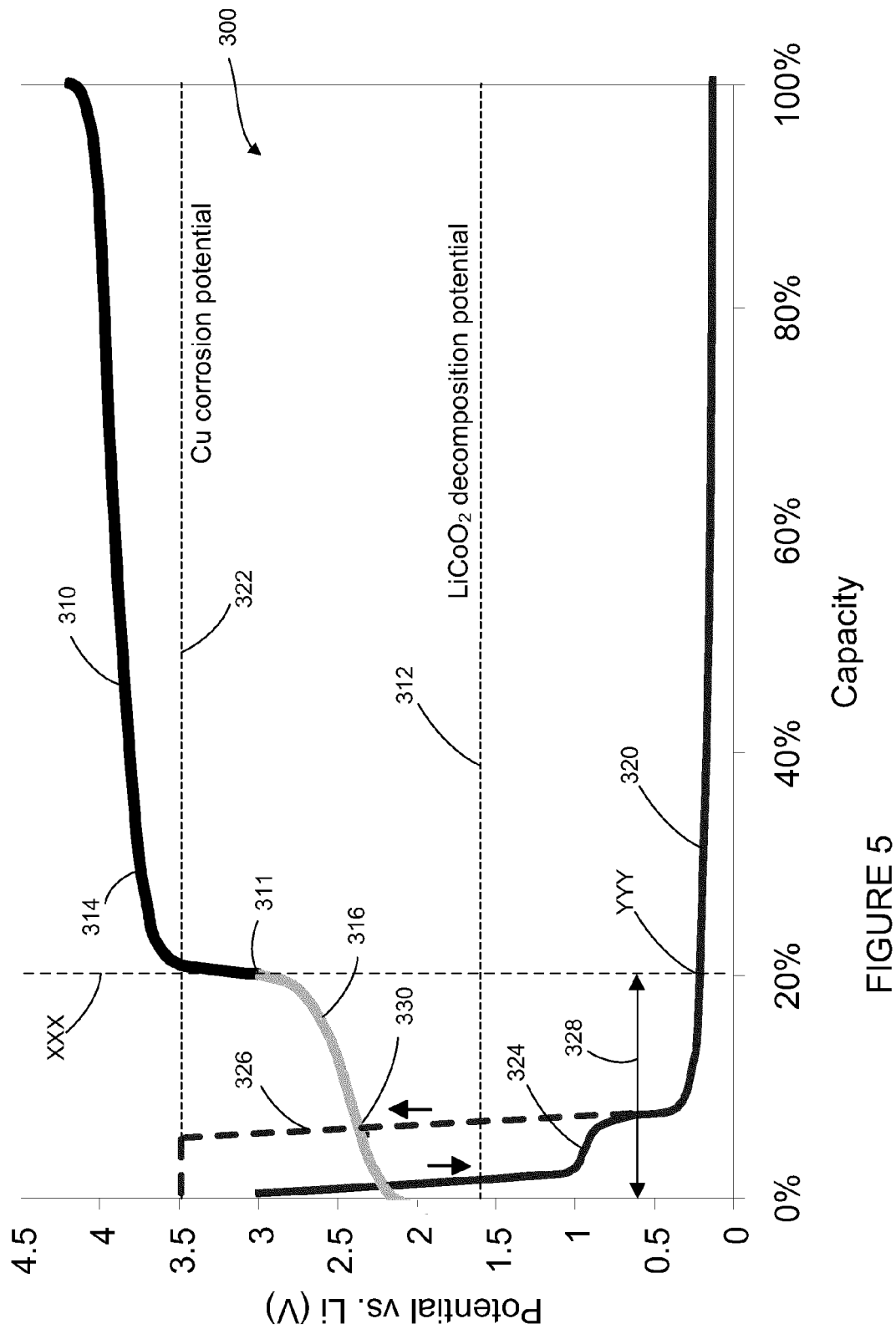
FIG. 5 is a graph illustrating the theoretical charging and discharging behavior for a lithium-ion battery such as that shown in FIG. 3.

FIG. 5 is a graph 300 illustrating the theoretical charging and discharging behavior for a lithium-ion battery constructed in accordance with an exemplary embodiment such as that shown and described with regard to FIG. 3. Curve 310 represents the electrode potential versus a lithium reference electrode for a positive electrode (e.g., positive electrode 210) that includes an aluminum current collector having a $LiCoO_2$ primary active material and a secondary active material provided thereon.

The secondary active material is selected to provide significant charging/discharging capacity below the corrosion potential (shown as dashed line 322) of the negative current collector and above the decomposition potential (shown as dashed line 312) of the $LiCoO_2$ primary active material. According to an exemplary embodiment, the secondary active material is $V_6O_{13}$ or $LiMn_2O_4$. According to various other exemplary embodiments, the secondary active material may be selected from the following materials and combinations thereof: $V_2O_5$, $LiMn_2O_4$, $V_6O_{13}$, $LiM_xMn_{(2-x)}O_4$ (spinel) where M is metal (including Li), $Li_4Ti_5O_{12}$, $Li_xVO_2$, $V_3O_8$, $MoO_3$, $TiS_2$, $WO_2$, $MoO_2$, and $RuO_2$.

Curve 320 represents the electrode potential versus a lithium reference electrode for a negative electrode that includes a copper current collector having a carbonaceous active material (i.e., carbon) and a lithium patch provided thereon. The difference between curves 310 and 320 is representative of the overall cell voltage of the battery.

It should be noted that the theoretical charging and discharge behavior for the negative electrode is believed to be qualitatively similar to that shown in FIG. 5 for a copper current collector having a $Li_4Ti_5O_{12}$ active material provided thereon (as opposed to a carbon active material), with the relatively flat portion of the curve 320 being shifted upward to a level of approximately 1.57 volts (in contrast to the approximately 0.1 volts for the carbon active material).

Upon initial charging, the battery experiences an irreversible loss of capacity due to the formation of a passive layer on the negative electrode, which may be referred to as a solid-electrolyte interface ("SEI"). The irreversible loss of capacity is shown as a ledge or shelf 324 in curve 320. The lithium patch is provided so as to compensate for the irreversible loss of capacity and to provide lithium to the second active material in the event of discharge to a voltage approaching zero. For example, as shown in FIG. 5, the relative capacity provided by the lithium patch is shown by arrow 328.

As shown in FIG. 5, the initial state of the cell, after it is filled with electrolyte and allowed to equilibrate, is indicated by dashed line XXX. The potential of the positive electrode, as shown by curve 310, is approximately 3 volts (shown as point 311). The potential of the negative electrode, as shown by curve 320, is approximately 0.1 volts (shown as point YYY). When the cell is charged, the potentials of the positive and negative electrodes progress to the right along curves 310 and 320, respectively. When the cell is discharged, the potentials of the positive and negative electrode potentials progress toward the left.

The charging/discharging behavior of the primary and secondary active materials (e.g., primary active material 216 and secondary active material 218) provided on the positive current collector are shown in FIG. 5 as two portions 314, 316 of curve 310. Portion 314 of curve 310 represents the charging/discharging behavior of the positive electrode due to the doping and undoping of the primary active material (i.e., $LiCoO_2$), while portion 316 of curve 310 represents the charging/discharging behavior of the positive electrode due to the doping and undoping of the secondary active material (i.e., $V_6O_{13}$, $LiMn_2O_4$, etc.).

Upon discharging the battery to a point approaching zero volts, the negative electrode potential follows a path designated by line 326. However, because the secondary active material is chosen to have significant charging/discharging capacity below the corrosion potential of the negative current collector and above the decomposition potential of the $LiCoO_2$ primary active material, the zero voltage crossing potential (shown as point 330) is below the corrosion potential of the negative current collector and above the decomposition potential of the $LiCoO_2$ primary active material, thus avoiding corrosion of the negative current collector (and potentially of the battery case) and any associated loss of battery charging capacity.

It is intended that a lithium-ion battery such as that described herein may be fully discharged while the materials for both electrodes, including their corresponding current collectors, are stable (e.g., corrosion of the current collectors and/or the decomposition of active material may be avoided, etc.). One potential advantageous feature of such an arrangement is that the occurrence of reduced device functionality (i.e., the need to recharge more frequently) and corrosion of the current collectors and battery case (with the incumbent possibility of leaking potentially corrosive and toxic battery contents) may be reduced or avoided. Another advantageous feature of such an arrangement is that the battery may be repeatedly cycled (i.e., charged and discharged) to near-zero-voltage conditions without significant decline in battery performance.

Various advantageous features may be obtained by utilizing batteries such as those shown and described herein. For example, use of such batteries may eliminate the need to utilize circuitry to disconnect batteries approaching near-zero voltage conditions. By not utilizing circuitry for this function, volume and cost reductions may be obtained.

According to an exemplary embodiment, lithium-ion batteries such as those described above may be used in conjunction with medical devices such as medical devices that may be implanted in the human body (referred to as "implantable medical devices" or "IMD's").

Figure 6:
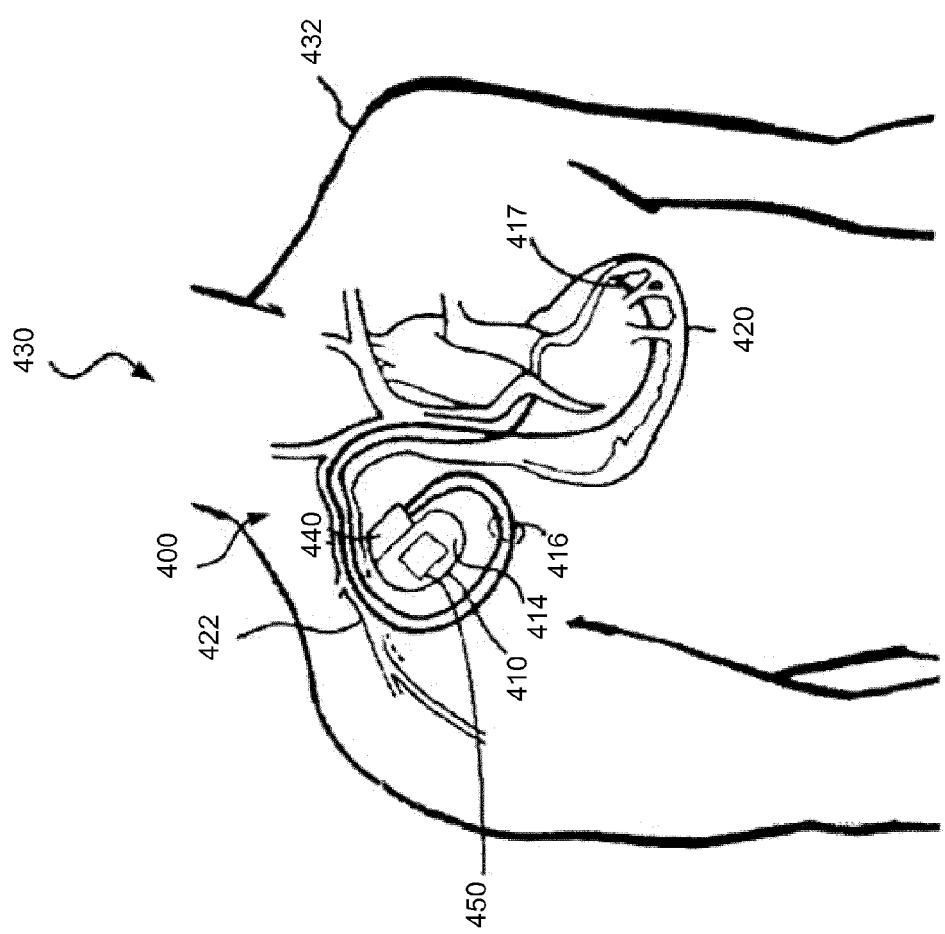
FIG. 6 is a schematic view of a system in the form of an implantable medical device implanted within a body or torso of a patient.

FIG. 6 illustrates a schematic view of a system 400 (e.g., an implantable medical device) implanted within a body or torso 432 of a patient 430. The system 400 includes a device 410 in the form of an implantable medical device that for purposes of illustration is shown as a defibrillator configured to provide a therapeutic high voltage (e.g., 700 volt) treatment for the patient 430.

The device 410 includes a container or housing 414 that is hermetically sealed and biologically inert according to an exemplary embodiment. The container may be made of a conductive material. One or more leads 416 electrically connect the device 410 and to the patient's heart 420 via a vein 422. Electrodes 417 are provided to sense cardiac activity and/or provide an electrical potential to the heart 420. At least a portion of the leads 416 (e.g., an end portion of the leads shown as exposed electrodes 417) may be provided adjacent or in contact with one or more of a ventricle and an atrium of the heart 420.

The device 410 includes a battery 440 provided therein to provide power for the device 410. According to another exemplary embodiment, the battery 440 may be provided external to the device or external to the patient 430 (e.g., to allow for removal and replacement and/or charging of the battery). The size and capacity of the battery 440 may be chosen based on a number of factors, including the amount of charge required for a given patient's physical or medical characteristics, the size or configuration of the device, and any of a variety of other factors. According to an exemplary embodiment, the battery is a 500 mAh battery. According to another exemplary embodiment, the battery is a 300 mAh battery. According to various other exemplary embodiments, the battery may have a capacity of between approximately 10 and 1000 mAh.

According to other exemplary embodiments, more than one battery may be provided to power the device 410. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

Figure 7:
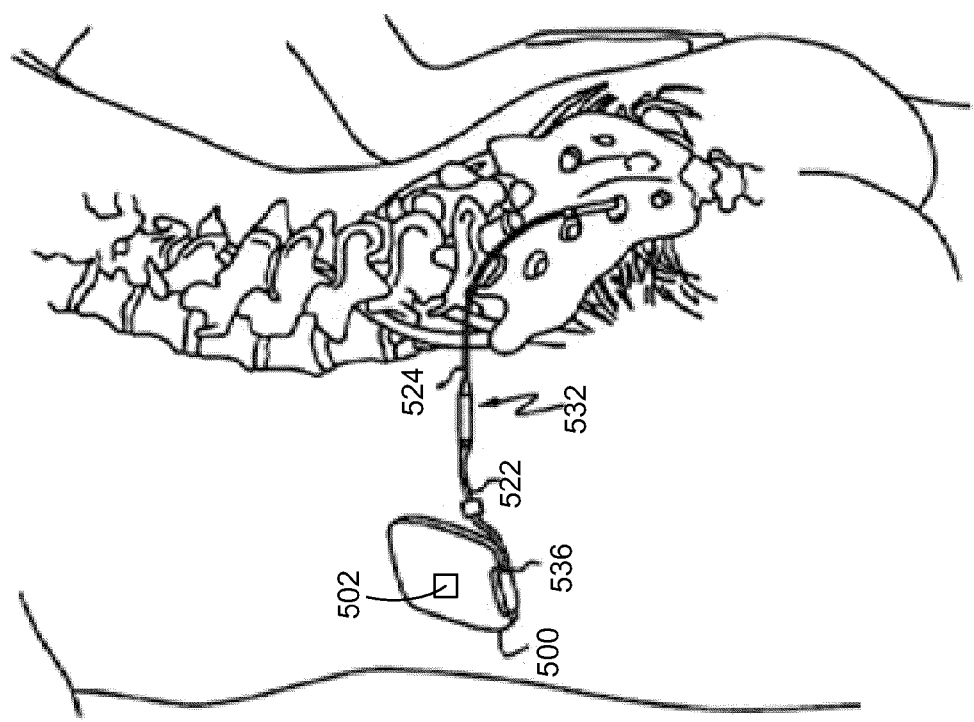
FIG. 7 is schematic view of another system in the form of an implantable medical device.

According to another exemplary embodiment shown in FIG. 7, an implantable neurological stimulation device 500 (an implantable neuro stimulator or INS) may include a battery 502 such as those described above with respect to the various exemplary embodiments. Examples of some neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 500 includes a lead extension 522 and a stimulation lead 524. The stimulation lead 524 is one or more insulated electrical conductors with a connector 532 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 532 can be connected directly to the INS 500 (e.g., at a point 536), typically the lead connector 532 is connected to a lead extension 522. The lead extension 522, such as a Model 7495 available from Medtronic, is then connected to the INS 500.

Implantation of an INS 500 typically begins with implantation of at least one stimulation lead 524, usually while the patient is under a local anesthetic. The stimulation lead 524 can either be percutaneously or surgically implanted. Once the stimulation lead 524 has been implanted and positioned, the stimulation lead's 524 distal end is typically anchored into position to minimize movement of the stimulation lead 524 after implantation. The stimulation lead's 524 proximal end can be configured to connect to a lead extension 522.

The INS 500 is programmed with a therapy and the therapy is often modified to optimize the therapy for the patient (i.e., the INS may be programmed with a plurality of programs or therapies such that an appropriate therapy may be administered in a given situation). In the event that the battery 502 requires recharging, an external lead (not shown) may be used to electrically couple the battery to a charging device or apparatus.

A physician programmer and a patient programmer (not shown) may also be provided to allow a physician or a patient to control the administration of various therapies. A physician programmer, also known as a console programmer, uses telemetry to communicate with the implanted INS 500, so a clinician can program and manage a patient's therapy stored in the INS 500, troubleshoot the patient's INS 500 system, and/or collect data. An example of a physician programmer is a Model 7432 Console Programmer available from Medtronic. A patient programmer also uses telemetry to communicate with the INS 500, so the patient can manage some aspects of her therapy as defined by the clinician. An example of a patient programmer is a Model 7434 Itrel® 3 EZ Patient Programmer available from Medtronic.

Referring to FIGS. 8-20, a battery may include an auxiliary electrode with a current collector and a third active material. The auxiliary electrode is configured for repeated selective electrical connection to the negative electrode when a predetermined condition is met. The third active material of the auxiliary electrode has a charging and discharging capacity below a corrosion potential of the current collector of the negative electrode and above a decomposition potential of the first active material.

Figure 8:
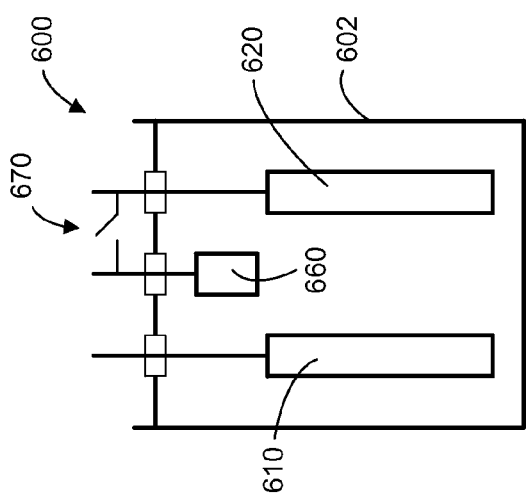
FIG. 8 is a schematic view of a portion of a lithium-ion battery having an auxiliary negative electrode according to an exemplary embodiment.

With reference to FIG. 8, a schematic view of a portion of a lithium-ion battery 600 having a case 602 is shown according to an exemplary embodiment. According to an exemplary embodiment, the battery 600 has a rating of between approximately 10 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery.

The battery 600 includes at least one positive electrode 610, at least one negative electrode 620, and an auxiliary electrode 660 that may be selectively electrically connected or coupled to the negative electrode 620 (e.g., by a switch 670, and according to another exemplary embodiment, according to a diode or other device). The auxiliary electrode 660, while being shown in the headspace of the battery 600, may be provided in other locations as may be desired. Also, it should be noted that one of the positive electrode 610 and negative electrode 620 may be coupled to the case 602 (e.g., as opposed to being electrically isolated from the case) according to other exemplary embodiments. The electrodes may be provided as flat or planar components of the battery 600, may be wound in a spiral or other configuration, or may be provided in a folded configuration. For example, the electrodes may be wrapped around a relatively rectangular mandrel such that they form an oval wound coil for insertion into a relatively prismatic battery case. According to other exemplary embodiments, the battery may be provided as a button cell battery, a thin film solid state battery, or as another lithium-ion battery configuration.

According to an exemplary embodiment, the negative electrode 620 and the auxiliary electrode 660 are provided within the battery such that they are electrically isolated from one another. For example, an insulative material (e.g., a porous polymeric material (e.g., polypropylene, polyethylene, etc.), a glass, or a ceramic material) may be provided between the negative electrode 620 and the auxiliary electrode 660.

Figure 9:
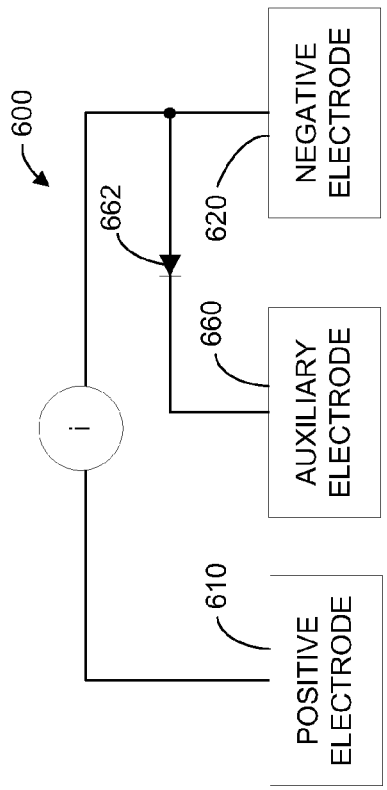
FIG. 9 is a schematic view of the lithium-ion battery shown in FIG. 8 according to one exemplary embodiment.

The auxiliary electrode 660 may be selectively electrically connected or coupled to the negative electrode 620 by way of a connection provided external to the battery. The selective electrical connection and disconnection between the auxiliary electrode 660 and the negative electrode 620 may be accomplished in any of a variety of ways. For example, FIG. 9 illustrates a configuration in which the auxiliary electrode 660 and negative electrode 620 are connected by way of a diode 662 (or a plurality of diodes according to another embodiment) placed between the auxiliary electrode 660 and the negative electrode 620. According to this exemplary embodiment, the diode or series of diodes may be configured such that an electrical connection between the auxiliary electrode 660 and negative electrode 620 occurs only when the potential difference between the negative electrode 620 and the auxiliary electrode 660 exceeds a predetermined threshold value (e.g., approximately 0.3 volts according to an exemplary embodiment and between approximately 0.1 and 0.5 volts according to another exemplary embodiment). The auxiliary electrode 660 and the negative electrode 620 may be disconnected (i.e., electrically isolated) whenever the potential difference between the negative electrode and the auxiliary electrode falls below the predetermined value. According to an exemplary embodiment, the diode 662 is a 0.3 volt diode. According to other exemplary embodiments, the diode 662 or series of diodes have a voltage of between approximately 0.2 and 0.7 volts. According to an exemplary embodiment, the potential difference at which the connection and disconnection of the auxiliary electrode 660 and the negative electrode 620 occurs is selected such that the potential of the auxiliary electrode material always remains above its reductive decomposition potential.

Figure 10:
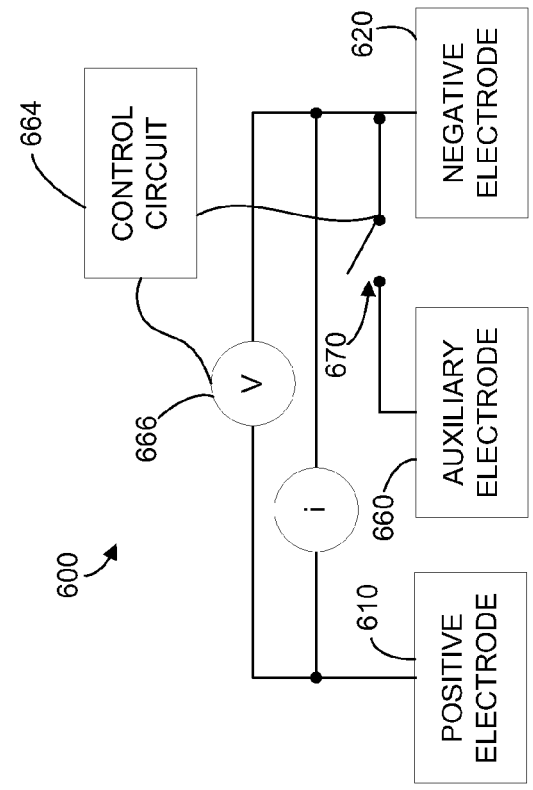
FIG. 10 is a schematic view of the lithium-ion battery shown in FIG. 8 according to another exemplary embodiment.

FIG. 10 illustrates a configuration for the battery 600 according to another exemplary embodiment. A control circuit 664 (which may be implemented in hardware, software, or firmware, for example) receives input signals from a voltmeter 666 which measures the voltage between the positive electrode 610 and the negative electrode 620. When the voltage difference between the positive electrode 610 and the negative electrode 620 falls below a predetermined threshold (e.g., 1.8 volts), the control circuit instructs a switch 670 to close, thereby electrically connecting the auxiliary electrode 660 to the negative electrode 620. The switch 670 may be instructed to open (thus electrically disconnecting the negative electrode 620 and the auxiliary electrode 660) when the voltage difference between the positive electrode 610 and the negative electrode 620 exceeds the predetermined threshold.

While FIGS. 9 and 10 illustrate two embodiments in which the auxiliary electrode 660 would be electrically connected to the negative electrode 620, it should be understood by those of skill in the art that any of a variety of other mechanisms may be utilized in order to electrically connect the auxiliary electrode to the negative electrode when a predetermined condition has been satisfied. As such, the embodiment shown in FIGS. 9 and 10 should not be understood to be limiting to the scope of the invention as described in the appended claims.

Figure 11:
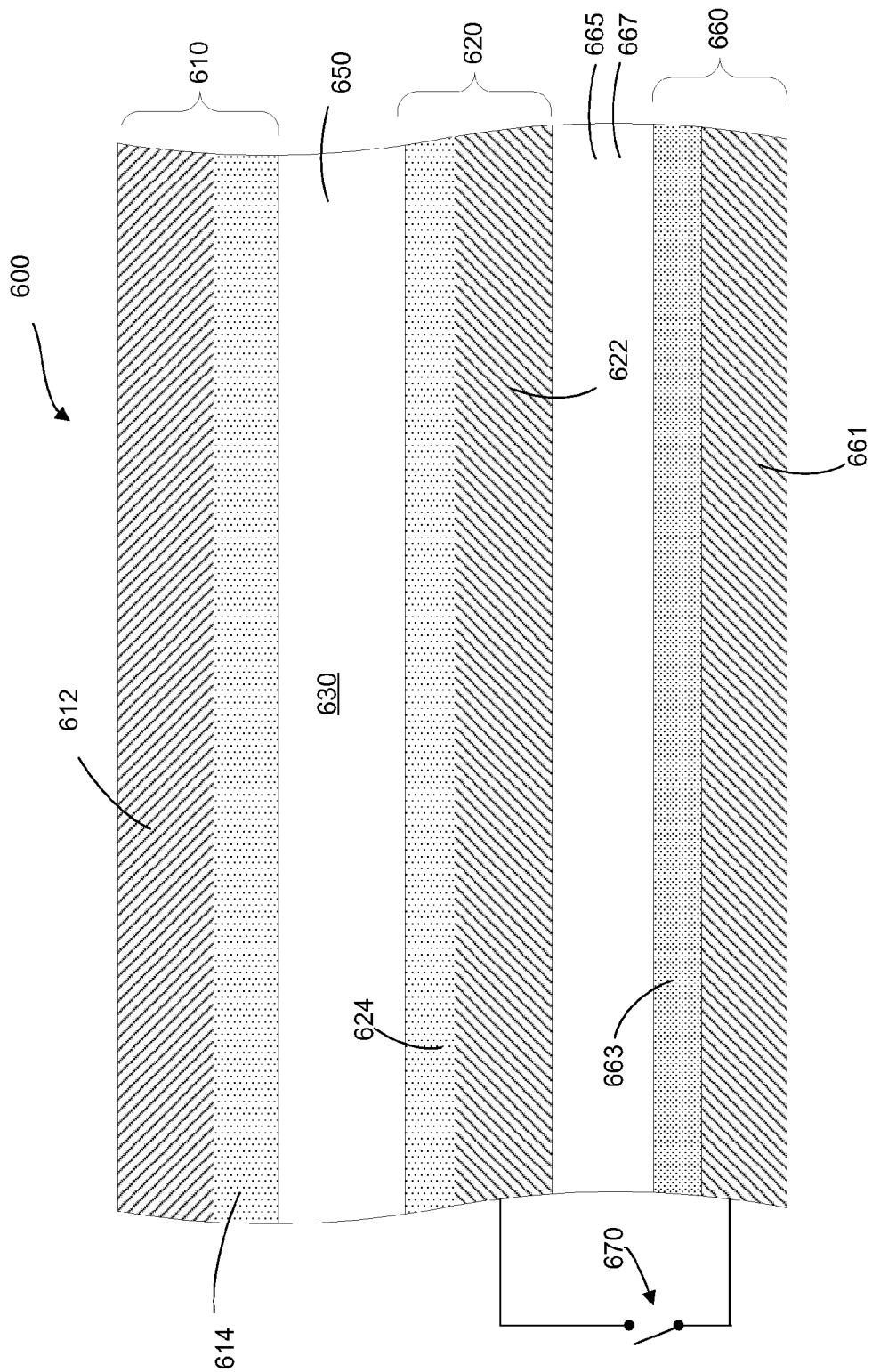
FIG. 11 is a schematic cross-sectional view of a portion of the lithium-ion battery shown in FIG. 8 according to one exemplary embodiment.

FIG. 11 is a schematic cross-sectional view of a portion of the battery 600 shown in FIG. 8. The battery 600 includes a positive electrode 610, a negative electrode 620, and an auxiliary electrode 660. The auxiliary electrode 660 may be selectively electrically coupled or connected to the negative electrode 620 by virtue of a switch 670 or other means. It should be understood that switch 670 may be a mechanism such as, but not limited to, those devices such as in the embodiments shown in FIGS. 9 and 10.

The positive electrode 610 includes a current collector 612 made of a conductive material such as a metal. According to an exemplary embodiment, the current collector 612 comprises aluminum or an aluminum alloy. According to an exemplary embodiment, the thickness of the current collector 612 is between approximately 5 µm and 75 µm. According to a particular exemplary embodiment, the thickness of the current collector 612 is approximately 20 µm. It should also be noted that while the positive current collector 612 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 612 has a layer of active material 614 provided thereon (e.g., coated on the current collector). While FIG. 8 shows that the active material 614 is provided on only one side of the current collector 612, it should be understood that a layer of active material similar or identical to that shown as active material 614 may be provided or coated on both sides of the current collector 612.

According to an exemplary embodiment, the active material 614 is a material or compound that includes lithium. The lithium included in the active material 614 may be doped and undoped during discharging and charging of the battery, respectively. According to an exemplary embodiment, the active material 614 is lithium cobalt oxide ($LiCoO_2$). According to another exemplary embodiment, the positive active material is of the form $LiCo_xNi_{(1-x)}O_2$, with x being between approximately 0.05 and 0.8. According to another exemplary embodiment, the primary active material is of the form $LiM_xCo_yNi_{(1-x-y)}O_2$, where M is aluminum or titanium, x is between approximately 0.05 and 0.3 and y is between approximately 0.1 and 0.3. According to another exemplary embodiment, the positive active material is $LiCo_xMn_yNi_zO_2$ or $LiNi_xCo_yAl_zO_2$. According to other exemplary embodiments, the primary active material may include $LiMn_2O_4$.

A binder material may also be utilized in conjunction with the active material 614. For example, according to an exemplary embodiment, the active material may include a conductive additive such as carbon black and a binder such as polyvinylidine fluoride (PVDF) or an elastomeric polymer.

The negative current collector 622 included as part of the negative electrode 620 is made of a conductive material such as a metal. According to an exemplary embodiment, the current collector 622 is copper or a copper alloy. According to another exemplary embodiment, the current collector 622 is titanium or a titanium alloy. According to another exemplary embodiment, the current collector 622 is nickel or a nickel alloy. According to another exemplary embodiment in which the negative active material 624 is not carbon, the current collector 622 is aluminum or an aluminum alloy. It should also be noted that while the negative current collector 622 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

According to an exemplary embodiment, the thickness of the current collector 622 is between approximately 100 nm and 100 µm. According to a particular exemplary embodiment, the thickness of the current collector 622 is between approximately 5 μm and 25 μm. According to a particular exemplary embodiment, the thickness of the current collector is approximately 10 μm.

The negative current collector 622 has a layer of active material 624 provided thereon. While FIG. 8 shows that the active material 624 is provided on only one side of the current collector 622, it should be understood that a layer of active material similar or identical to that shown may be provided or coated on both sides of the current collector 622. According to an exemplary embodiment, the active material 624 may include a conductive additive such as carbon black and a binder such as polyvinylidine fluoride (PVDF) or an elastomeric polymer.

According to an exemplary embodiment the active material 624 is a carbonaceous material (e.g., carbon such as graphite). According to another exemplary embodiment, the active material 624 is a lithium titanate material such as $Li_4Ti_5O_{12}$. One advantage of using a lithium titanate material in place of a carbonaceous material is that it is believed that the use of a lithium titanate material allows for charging and discharging of the battery at higher rates than is capable using carbonaceous materials.

Other lithium titanate materials which may be suitable for use as the active material 624 may include one or more of include the following lithium titanate spinel materials: $H_x Li_{y-x}TiO_xO_4$, $H_xLi_{y-x}TiO_xO_4$, $Li_4M_xTi_{5-x}O_{12}$, $Li_xTi_yO_4$, $Li_{x-}Ti_yO_4$, $Li_4[Ti_{1.67}Li_{0.33-y}M_y]O_4$, $Li_2TiO_3$, $Li_4Ti_{4.75}V_{0.25}O_{12}$, $Li_4Ti_{4.75}Fe_{0.25}O_{11.88}$, and $Li_4Ti_{4.5}Mn_{0.5}O_{12}$, and $LiM'M''XO_4$ (where M' is a transition metal, M'' is an optional three valent non-transition metal, and X is zirconium, titanium, or a combination of these two, and where M' is nickel, cobalt, iron, manganese, vanadium, copper, chromium, molybdenum, niobium, or combinations thereof). Note that such lithium titanate spinel materials may be used in any state of lithiation (e.g., $Li_{4+x}Ti_5O_{12}$, where 0≤x≤3).

One advantage of using a lithium titanate material instead of a carbonaceous material is that it is believed that the use of a lithium titanate material allows for charging and discharging of the battery at higher rates than is capable using carbonaceous materials. According to other exemplary embodiments, the negative active material 624 may be carbon, $Li_xAl$, $Li_xSn$, $Li_xSi$, $Li_xSnO$, metal nanoparticle composites (e.g., including $Li_xAl$, $Li_xSn$, $Li_xSi$, or $Li_xSnO$), or carbon-coated lithium titanate. Lithium titanate materials are also believed to offer superior cycle life because they are so called "zero-strain" materials. Zero strain materials have crystal lattices which do not experience shrinkage or contraction with lithium doping/de-doping, making them free from strain-related degradation mechanisms.

According to various exemplary embodiments, the thickness of the active material 624 is between approximately 0.1 μm and 3 mm. According to other exemplary embodiments, the thickness of the layer of active material 624 may be between approximately 25 μm and 300 μm. According to a particular exemplary embodiment, the thickness of the active material 624 is approximately 75 μm.

The auxiliary electrode 660 includes a current collector 661 that is made of a conductive material such as a metal. According to an exemplary embodiment, the current collector 661 is titanium or a titanium alloy. According to another exemplary embodiment, the current collector 661 may be aluminum or an aluminum alloy. According to other exemplary embodiments, the current collector 661 may be nickel, stainless steel, or another suitable metal material. It should also be noted that while the current collector 661 has been illustrated and described as being a thin foil material, the current collector may have any of a variety of configurations according to various exemplary embodiments. For example, the current collector may be a grid such as a mesh grid, and an expanded metal grid, a photochemically etched grid, or the like.

According to an exemplary embodiment, the thickness of the current collector 661 is between approximately 10 and 40 μm. According to another exemplary embodiment, the thickness of the current collector is between approximately 10 μm and 20 μm. According to a particular exemplary embodiment, the thickness of the current collector 661 is approximately 10 μm.

The current collector 661 has a layer of active material 663 provided thereon. While FIG. 11 shows that the active material 663 is provided on only one side of the current collector 662, it should be understood that a layer of active material similar or identical to that shown may be provided or coated on both sides of the current collector 661.

The active material 663 is a material that is selected to have relatively significant charge and discharge capacity below the corrosion potential of the material used for the negative current collector 622 provided as part of the negative electrode 620 and above the decomposition potential of the active material 614 provided on the positive current collector 612. The active material 663 is also selected to be stable over its full potential-composition range in the electrolyte. For example, according to an exemplary embodiment in which the negative current collector 622 comprises copper, for which the corrosion potential is approximately 3.5 volts, the active material 663 includes significant charge and discharge capacity below 3.5 volts.

According to an exemplary embodiment in which the auxiliary electrode 660 is to be coupled to the negative electrode 620, the active material 663 must comprise lithium or be lithiated using a source of lithium (e.g., a lithium powder or a lithium patch, etc.) in electrical contact with the auxiliary electrode. According to an exemplary embodiment in which the active material 663 includes lithium, the active material is $LiMn_2O_4$. According to various other exemplary embodiments, the active material may be selected from the following materials and combinations thereof: $V_2O_5$, $V_6O_{13}$, $LiMn_2O_4$ (spinel), $LiM_xMn_{(2-x)}O_4$ (spinel) where M is metal (including Li) and x is between approximately 0.05 and 0.4, $Li_5Ti_4O_{12}$, $Li_xVO_2$ (where x is between approximately 0 and 1), $V_3O_8$, $MoO_3$, $TiS_2$, $WO_2$, $MoO_2$, and $RuO_2$, as well as their partially or fully lithiated counterparts.

Any lithium included in the active material 663 of the auxiliary electrode 660 has significant charge/discharge capacity that lies below the corrosion potential of the negative current collector 622 and/or any battery components to which it is electrically connected (e.g., the case) and above the decomposition potential of the positive electrode active material 614. The active material 663 contains electrochemically active lithium in the as-constructed state (completed cell including electrolyte). The lithium becomes significantly undoped at a potential below the corrosion potential for the negative current collector 622. In so doing, this material lowers the final potential of the negative electrode in the discharge state, so that the zero voltage crossing potential remains below the corrosion potential of the negative current collector and the battery case. The active material 663 may be capable of accepting the lithium when the battery is recharged.

It should be noted that while a variety of materials have been described above as being useful for active material 663, a variety of additional materials may be utilized in addition to or in place of such materials. For example, the active material 663 may comprise an oxide material such as one or more of $Li_xMoO_3$ (0<x≤2), $Li_xMoO_2$ (0<x≤1), $Li_xMo_2O_4$ (0<x≤2), $Li_xMnO_2$ (0<x≤1), $Li_xMn_2O_4$ (0<x≤2), $Li_xV_2O_5$ (0<x≤2.5), $Li_xV_3O_8$ (0<x≤3.5), $Li_xV_6O_{13}$ (0<x≤6 for $Li_xVO_{2.19}$ and 0<x≤3.6 for $Li_xVO_{2.17}$), $Li_xVO_2$ (0<x≤1), $Li_xWO_3$ (0<x≤1), $Li_xWO_2$ (0<x≤1), $Li_xTiO_2$ (anatase) (0<x≤1), $Li_xTi_2O_4$ (0<x≤2), $Li_xRuO_2$ (0<x≤1), $Li_xFe_2O_3$ (0<x≤2), $Li_xFe_3O_4$ (0<x≤2), $Li_xCr_2O$ (0<x≤3), $Li_xCr$ (0<x≤3.8), and $Li_xNi_yCo_{1-y}O_2$ (0<x≤1, 0.9<y≤1.00).

According to another exemplary embodiment, the active material 663 may comprise a sulfide material such as one or more of $Li_xV_2S_5$ (0<x≤4.8), $Li_xTaS_2$ (0<x≤1), $Li_xFeS$ (0<x≤1), $Li_xFeS_2$ (0<x≤1), $Li_xNbS_3$ (0<x≤2.4), $Li_xMoS_3$ (0<x≤3), $Li_xMoS_2$ (0<x≤1), $Li_xTiS_2$ (0<x≤1), $Li_xZrS_2$ (0<x≤1), $Li_xFe_{0.25}V_{0.75}S_2$ (0<x≤1), $Li_xCr_{0.75}V_{0.25}S_2$ (0<x≤0.65), and $Li_xCr_{0.5}V_{0.5}S_2$ (0<x≤1).

According to another exemplary embodiment, the active material 663 may comprise a selenide material such as one or more of $Li_xNbSe_3$ (0<x≤3), $Li_xVSe_2$ (0<x≤1), or various other materials such as, for example, $Li_xNiPS_3$ (0<x≤1.5) and $Li_xFePS_3$ (0<x≤1.5).

According to an exemplary embodiment in which the active material 663 does not include lithium in the as-constructed state (e.g., the active material 663 is $V_6O_{13}$), a mechanism must be provided to lithiate the active material 663. According to an exemplary embodiment, a mass or quantity of lithium (e.g., a lithium "patch") may be provided, as will be discussed in greater detail below.

Figure 12:
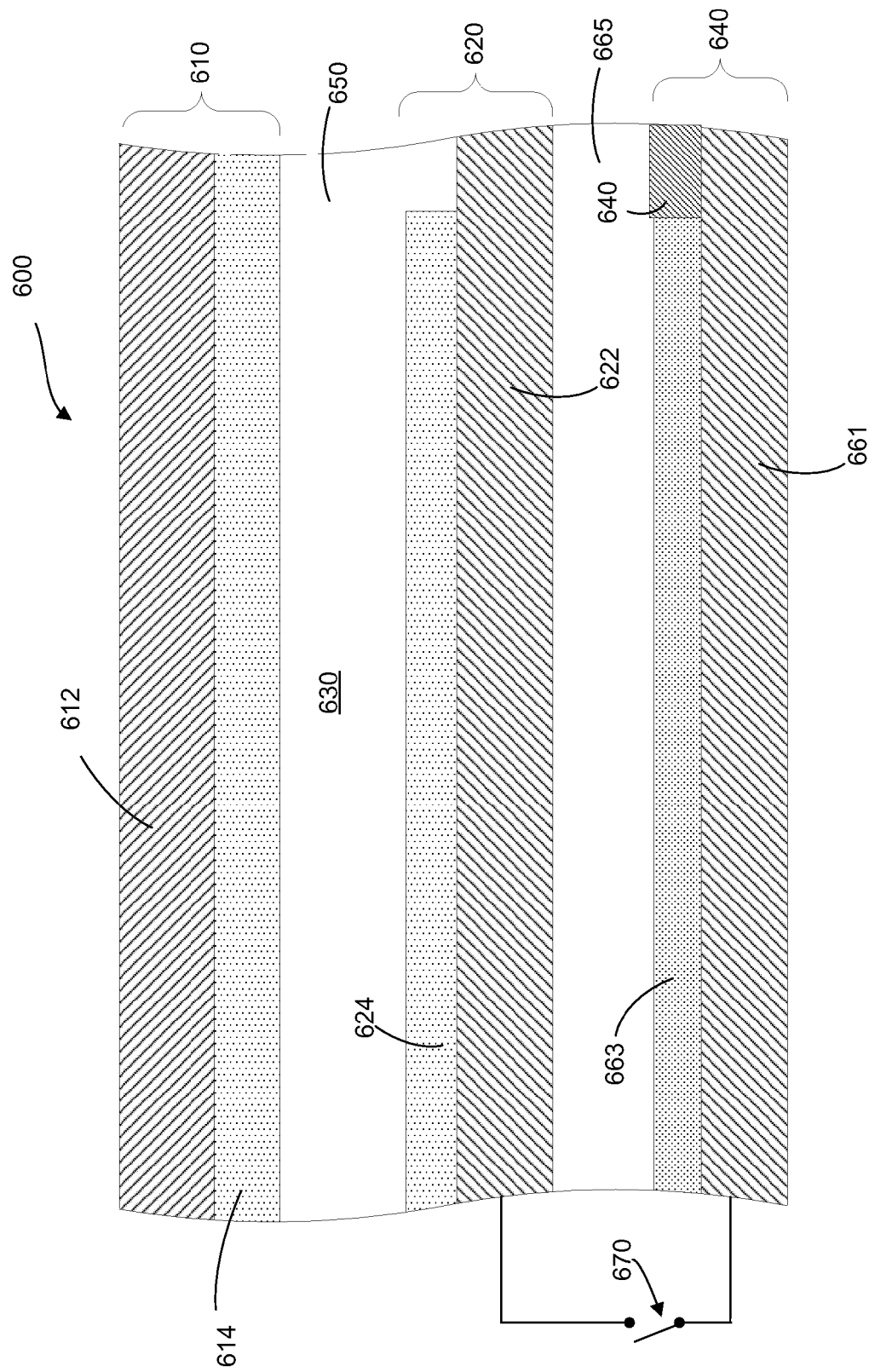
FIG. 12 is a schematic cross-sectional view of a portion of the lithium-ion battery shown in FIG. 8 according to another exemplary embodiment.

FIG. 12 shows a battery 600 according to another exemplary embodiment in which a mass or quantity of lithium 640 (e.g., a lithium patch) is provided in electrical contact with current collector 661 of the auxiliary electrode 660 to lithiate active material 663. Such a configuration corresponds to a situation in which the active material 663 is provided without including electrochemically active lithium (e.g., the active material 663 does not include lithium as it is coated on the negative current collector). One such exemplary embodiment involves the use of $V_2O_5$ for the active material 663. In contrast, FIG. 11 shows a configuration in which the active material 663 is provided as a lithiated material (e.g., $LiMn_2O_4$). In such an embodiment, a mass or quantity of lithium in contact with the current collector 661 of the auxiliary electrode 660 is not necessary.

The electrochemically active lithium may be provided in other locations in the negative electrode 620 and/or may have a different size or shape than that shown schematically in FIG. 12. For example, the electrochemically active lithium may be provided as a disc or as a rectangular piece of material coupled to the negative current collector. While the electrochemically active lithium is shown as being provided on a single side of the current collector 661 in FIG. 12 (e.g., as a lithium patch), separate lithium patches may be provided on opposite sides of the current collector 661. Further, multiple lithium patches may be provided on one or more of the sides of the current collector 661. In another example, the lithium may be provided elsewhere within the battery and connected (e.g., by a wire) to the current collector 661.

According to another exemplary embodiment, the electrochemically active or cyclable lithium may be added as finely divided or powdered lithium. Such powdered lithium includes a passive coating (e.g., a thin layer or film of lithium carbonate) provided thereon to reduce the reactivity of the powdered lithium with air and moisture. Such material may be mixed with the auxiliary electrode active material prior to application of the auxiliary electrode active material to fabrication of the cells or may be added as another separate active material layer. According to an exemplary embodiment, the finely divided or powdered lithium has a diameter of between approximately 1 μm and 100 μm, and according to a particular embodiment, between approximately 5 μm and 30 μm.

According to an exemplary embodiment in which a lithium patch 640 is utilized, the size of the lithium patch 640 is sufficient to fully lithiate the auxiliary electrode active material 663. According to an exemplary embodiment, the size of the lithium patch is between approximately 1.4 cm×1.4 cm×0.11 cm, which corresponds to approximately 0.013 grams (e.g., approximately 50 mAh). The specific size of the lithium patch may vary according to other exemplary embodiments (e.g., approximately 5% of the capacity of either the negative or positive electrode).

Figure 13:
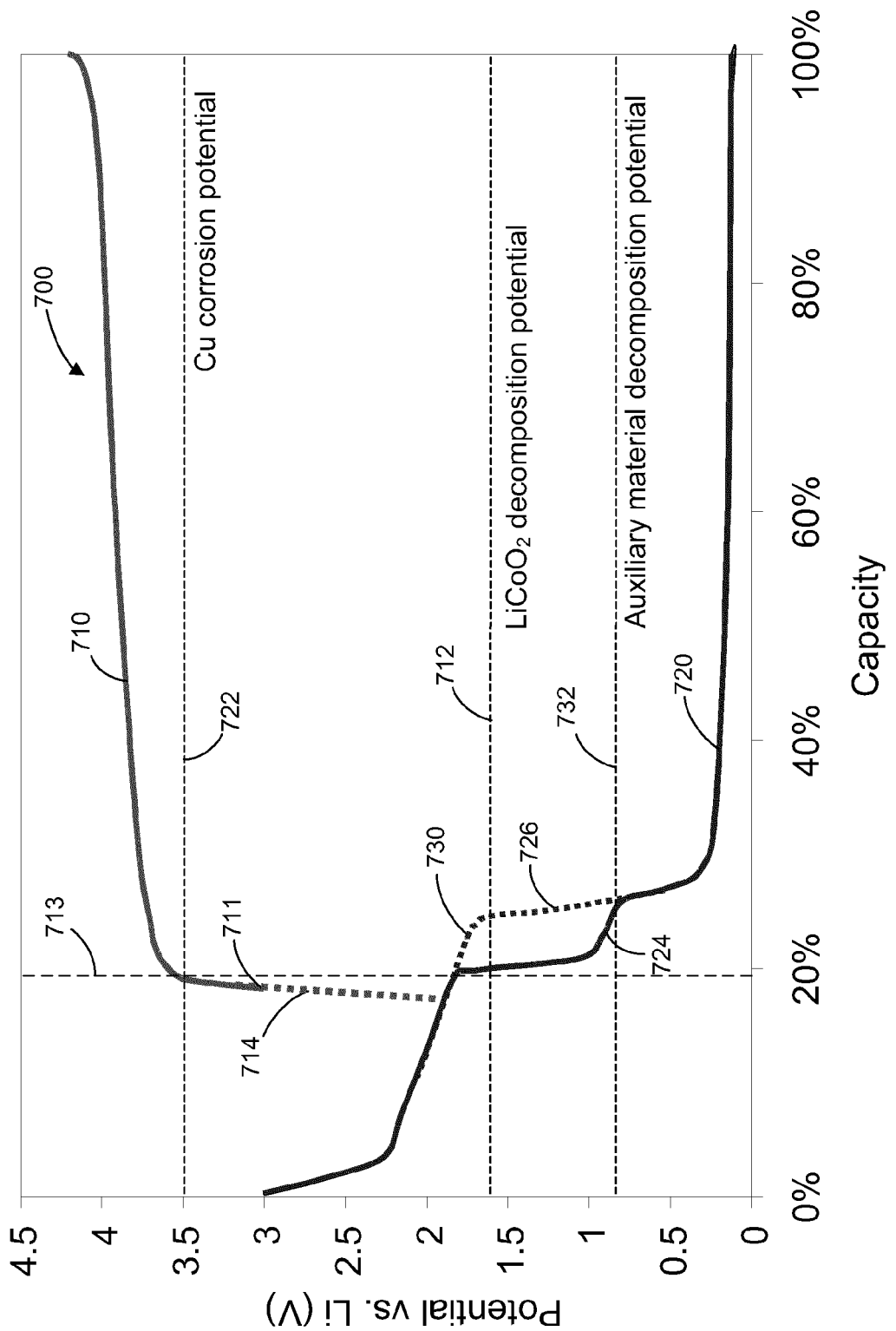
FIG. 13 is a graph illustrating the theoretical charging and discharging behavior for a lithium-ion battery such as that shown in FIG. 8.

FIG. 13 is a graph 700 illustrating the theoretical charging and discharging behavior for a lithium-ion battery constructed in accordance with an exemplary embodiment such as that shown and described with regard to FIGS. 8-12. Curve 710 represents the electrode potential versus a lithium reference electrode for a positive electrode (e.g., positive electrode 610) that includes an aluminum current collector having a $LiCoO_2$ primary active material provided thereon.

Curve 720 represents the electrode potential versus a lithium reference electrode for a negative electrode that includes a copper current collector having an active material (i.e., an active material 624 including, for example, a carbonaceous material such as carbon), a non-lithiated active material provided on an auxiliary electrode, and a lithium patch provided on the auxiliary electrode. The difference between curves 710 and 720 is representative of the overall cell voltage of the battery.

The active material provided on the auxiliary electrode is selected to provide significant charging/discharging capacity below the corrosion potential (shown as dashed line 722) of the negative current collector and above the decomposition potential (shown as dashed line 712) of the $LiCoO_2$ positive electrode active material, in addition to its ability to remain stable over its full potential-composition range in the electrolyte. According to an exemplary embodiment, the secondary active material is $V_6O_{13}$. According to various other exemplary embodiments, the secondary active material may be selected from the following materials and combinations thereof: $V_2O_5$, $V_6O_{13}$, $V_3O_8$, $MoO_3$, $TiS_2$, $WO_2$, $MoO_2$, and $RuO_2$.

It should be noted that the theoretical charging and discharge behavior for the negative electrode is believed to be qualitatively similar to that shown in FIG. 13 for a copper current collector having a $Li_4Ti_5O_{12}$ primary active material provided thereon (as opposed to a carbon active material), with the relatively flat portion of the curve 720 being shifted upward to a level of approximately 1.57 volts (in contrast to the approximately 0.1 volts for the carbon active material).

As shown in FIG. 13, when the battery is first constructed and electrolyte is provided within the battery, the potentials of the positive and negative electrodes begin at the point shown as dashed line 713. Upon initial charging to full capacity, the potential of the positive electrode, as shown by curve 710, increases from approximately 3.0 volts (shown as point 711) to a point above the corrosion potential of copper used to form the negative current collector (designated by dashed line 722). When the battery is subsequently discharged toward a zero voltage condition, the positive electrode potential will continue along a portion 714 of curve 710 to a point below approximately 3.0 volts (as shown by the dashed portion of curve 710 in FIG. 13).

The potential of the negative electrode decreases from a point below approximately 2.0 volts on initial charging to a point below the decomposition potential of the $LiCoO_2$ active material provided on the positive current collector (designated by dashed line 712 and below the decomposition potential of the secondary or auxiliary active material (designated by dashed line 732)). According to an exemplary embodiment, the corrosion potential of copper is approximately 3.5 volts, while the decomposition potential of the $LiCoO_2$ active material provided on the positive current collector is approximately 1.6 volts. According to another exemplary embodiment, the decomposition potential of the $LiCoO_2$ active material is approximately 1.35 volts.

The irreversible loss of capacity of the battery is shown as a ledge or shelf 724 in curve 720. Upon discharging the battery to a point approaching zero volts, the negative electrode potential follows a path designated by a dashed portion 726 of the curve 720. As the potential of the negative electrode moves above the decomposition potential of the auxiliary active material (designated as dash line 732), the auxiliary electrode is electrically connected to the negative electrode, remaining in electrical contact through complete discharging of the battery cell. Upon recharging the battery, the auxiliary electrode will be electrically disconnected from the negative electrode when the potential of the negative electrode moves below the decomposition potential of the auxiliary active material.

Because the active material on the negative current collector is chosen to have significant charging/discharging capacity below the corrosion potential of the negative current collector and above the decomposition potential of the $LiCoO_2$ primary active material, the zero voltage crossing potential (shown as point 730) is below the corrosion potential of the negative current collector and above the decomposition potential of the $LiCoO_2$ primary active material, thus avoiding corrosion of the negative current collector (and potentially of the battery case or any other battery component in electrical contact or communication with the negative electrode) and any associated loss of battery charging capacity. One advantageous feature of such an arrangement is that the battery may be repeatedly cycled (i.e., charged and discharged) to near-zero-voltage conditions without significant decline in battery performance.

It is intended that a lithium-ion battery such as that described herein may be fully discharged while the materials for both electrodes, including their corresponding current collectors, are stable (e.g., corrosion of the current collectors and/or the decomposition of active material may be avoided, etc.). One potential advantageous feature of such an arrangement is that the occurrence of reduced device functionality (i.e., the need to recharge more frequently) and corrosion of the current collectors and battery case (with the incumbent possibility of leaking potentially corrosive and toxic battery contents) may be reduced or avoided.

While the auxiliary electrode 660 has been described with respect to being selectively electrically connected or coupled to the negative electrode 620, according to another exemplary embodiment, an auxiliary electrode may be provided such that it may be selectively electrically connected or coupled to a positive electrode. FIGS. 14-18 show various views of a battery 1000 having a case 1002 including a positive electrode 1010, a negative electrode 1020, and an auxiliary electrode 1060 selectively electrically coupled or connected to the positive electrode (e.g., by a switch 1070, and according to another exemplary embodiment, according to a diode or other device). Also, it should be noted that one of the positive electrode 1010 and negative electrode 1020 may be coupled to the case 1002 (e.g., as opposed to being electrically isolated from the case) according to other exemplary embodiments. The auxiliary electrode 1060, while being shown in the headspace of the battery 1000, may be provided in other locations as may be desired. The various components shown in FIGS. 14-18 include reference numerals similar to those shown in FIGS. 8-12, with the reference numerals in FIGS. 14-18 being 400 away from the reference numerals shown in FIGS. 7-12 (e.g., negative electrode 620 shown in FIG. 9 corresponds to negative electrode 1020 shown in FIG. 15).

Figure 15:
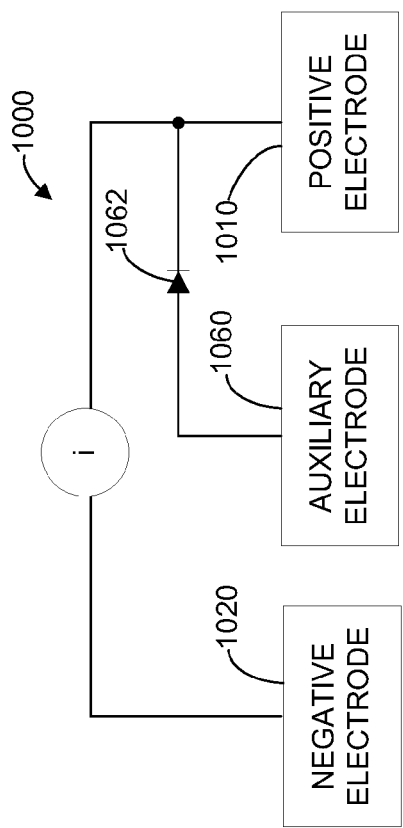
FIG. 15 is a schematic view of the lithium-ion battery shown in FIG. 14 according to one exemplary embodiment.
Figure 16:
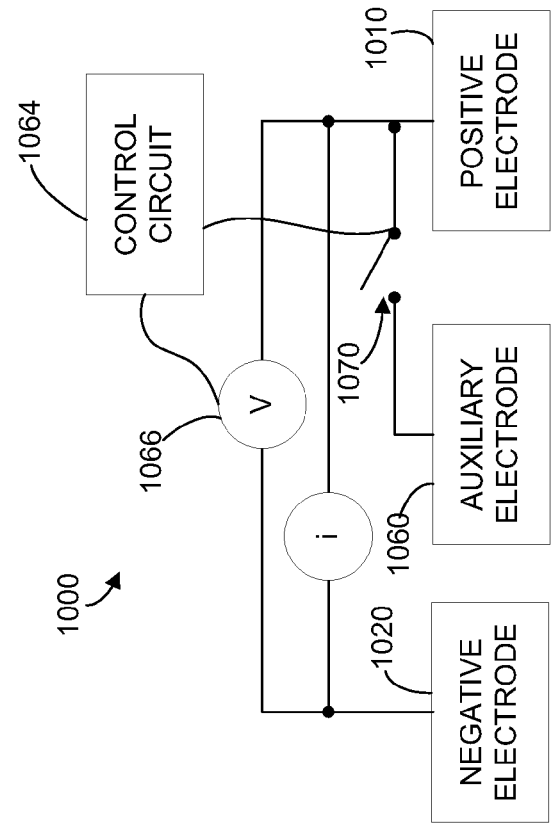
FIG. 16 is a schematic view of the lithium-ion battery shown in FIG. 14 according to another exemplary embodiment.
Figure 14:
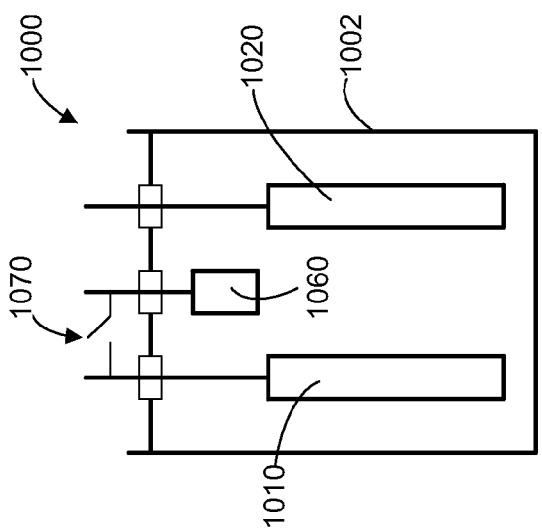
FIG. 14 is a schematic view of a portion of a lithium-ion battery having an auxiliary positive electrode according to an exemplary embodiment.
Figure 17:
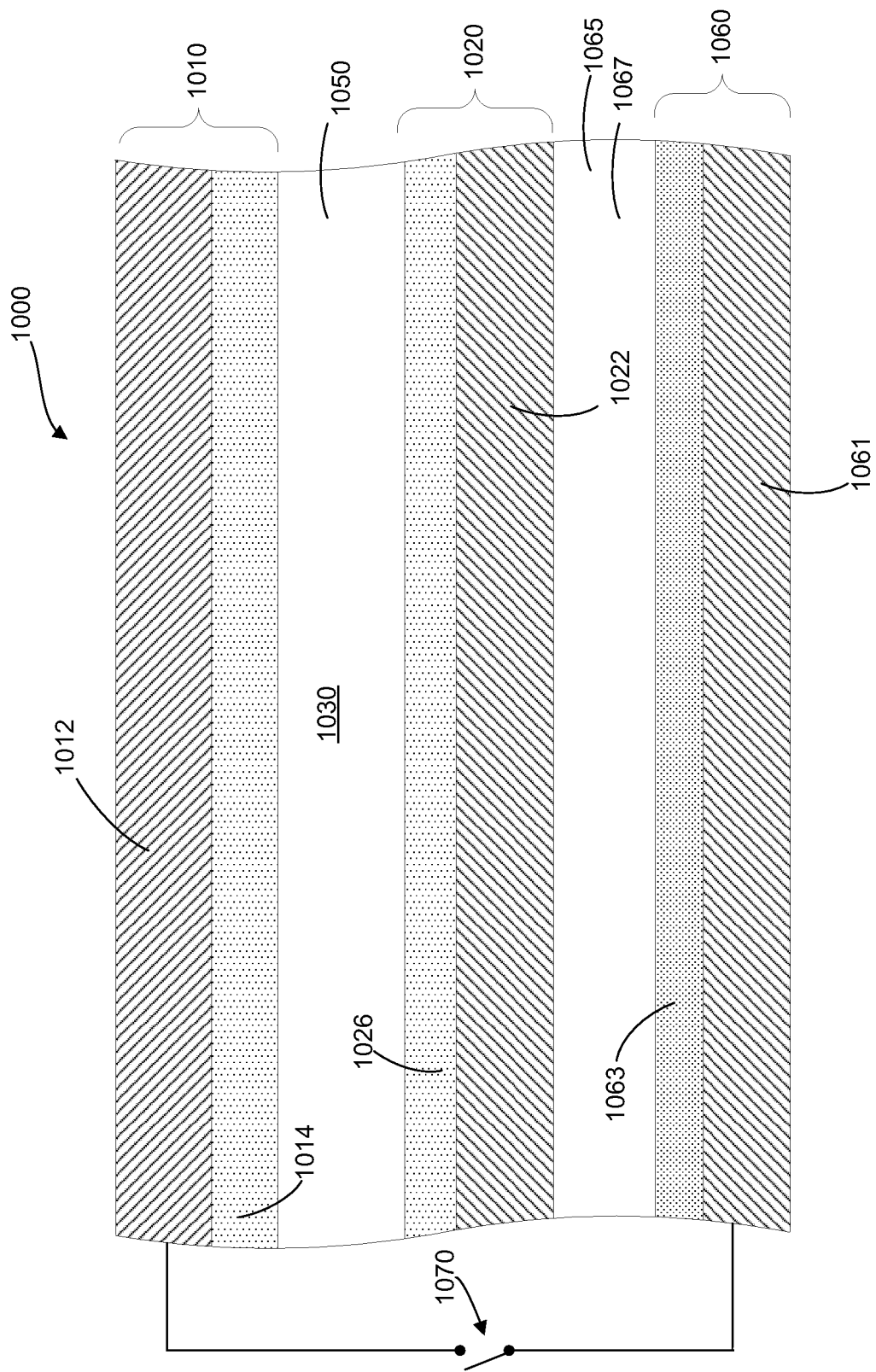
FIG. 17 is a schematic cross-sectional view of a portion of the lithium-ion battery shown in FIG. 14 according to one exemplary embodiment.
Figure 18:
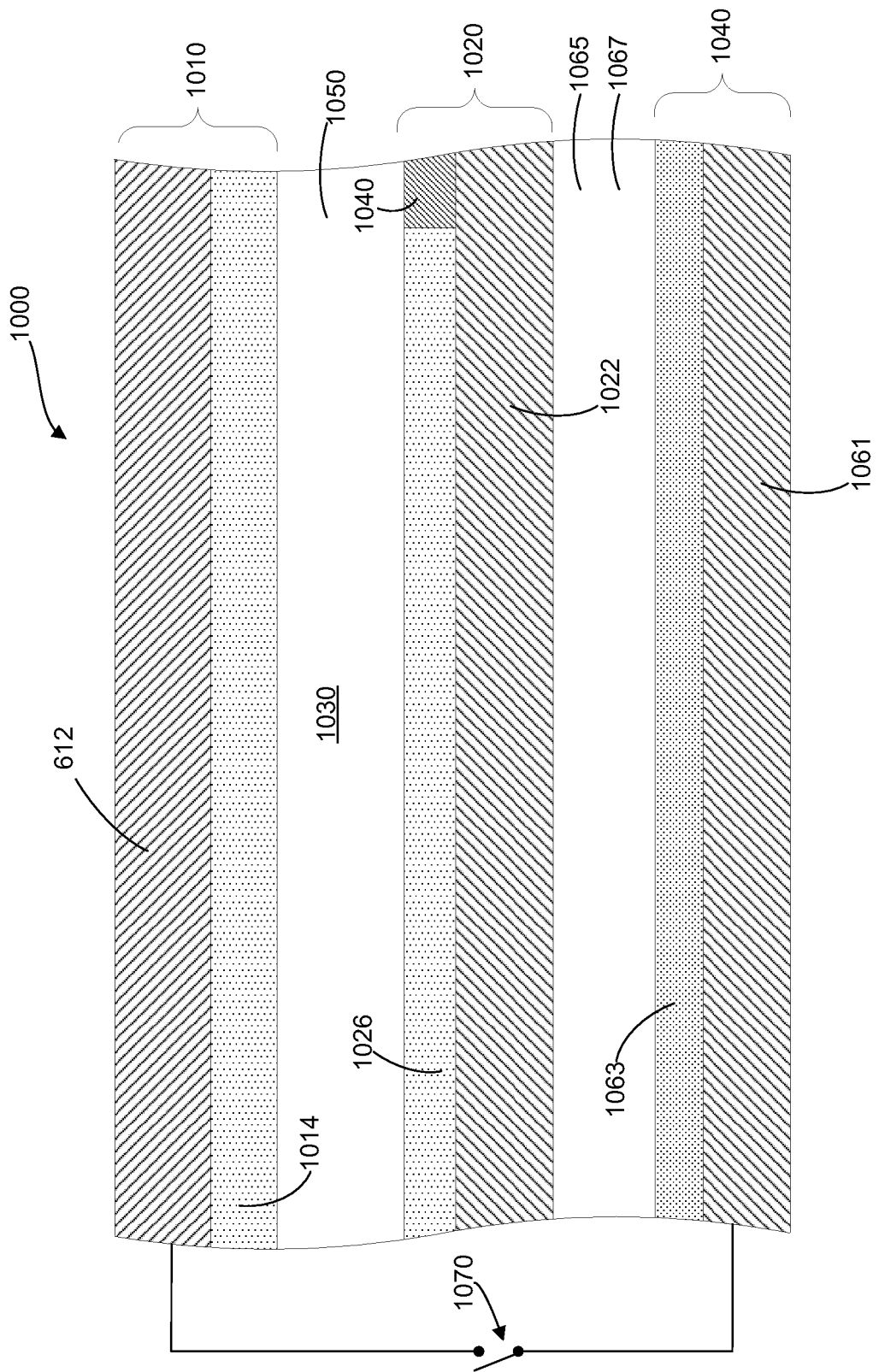
FIG. 18 is a schematic cross-sectional view of a portion of the lithium-ion battery shown in FIG. 14 according to another exemplary embodiment.

FIGS. 15-16 show exemplary schematic views of configurations for exemplary embodiments in which an auxiliary electrode 1060 is selectively electrically coupled to a positive electrode 1010. Such configurations are similar to those shown in FIGS. 9-10, with FIG. 15 representing the use of a diode 1062 and FIG. 16 representing the use of a control circuit 1064 which operates to close a switch 1070 to electrically connect the auxiliary electrode 1060 to the positive electrode 1010. As shown in FIGS. 17-18, a switch 1070 is provided which electrically connects the positive electrode 1010 to the auxiliary electrode 1060 external to the battery 1000. The auxiliary electrode 1060 is electrically isolated (using a separator 1065) from both the positive electrode 1010 and the negative electrode 1020, and an electrolyte 1067 may be provided. It should be noted that while FIGS. 17 and 18 show the auxiliary electrode as being adjacent to the negative electrode, the auxiliary electrode may be provided adjacent the positive electrode according to another exemplary embodiment. The various materials used for the components of the battery 1000 may be identical to those described with respect to the battery 600.

The active material 1063 provided on the current collector 1061 of the auxiliary electrode 1060 may be formed from a material similar to those described above, with the provision that such materials must be provided in their oxidized (i.e., de-lithiated) form. That is to say, the auxiliary electrode does not include an active material that utilizes lithium according to an exemplary embodiment in which the auxiliary electrode is configured for selective coupling and decoupling from the positive electrode. Further, it should be noted that according to an exemplary embodiment in which the auxiliary electrode is configured for selective coupling and decoupling from the positive electrode, the active material provided on the negative current collector must include lithium or be provided with a source of lithium (e.g., powdered lithium, a lithium patch, etc.) sufficient to compensate at minimum for the loss of lithium due to the formation of an SEI during initial charging (see, e.g., FIG. 17, in which a powdered lithium material is provided, and FIG. 18, in which a lithium patch is provided on the negative electrode).

It may be advantageous to provide a battery such as that shown as battery 1000 in FIGS. 14-18 for a variety of reasons. For example, the active material 1063 provided on the current collector 1061 of the auxiliary electrode 1060 may prevent the positive electrode from being pulled below its decomposition potential in a fully discharged cell (e.g., it may prevent decomposition of the active material 1014 provided on the current collector 1012 of the positive electrode 1010). This may protect the positive electrode in situations where, for example, the negative electrode (e.g., a carbon electrode) is pre-lithiated using the lithium patch in order to protect its potential from being pulled above the corrosion potential of the negative current collector 1022 of the negative electrode 1020. It may also be advantageous to provide a battery having an arrangement such as that shown in FIGS. 14-18 in the event that the active material applied to the auxiliary electrode is not stable (i.e., becomes oxidized) at the maximum potential of the positive electrode in a fully charged cell. In contrast, in situations in which the secondary active material is stable (i.e., does not become oxidized at the maximum potential of the positive electrode in a fully charged cell), it could be directly added to the positive electrode material.

Figure 19:
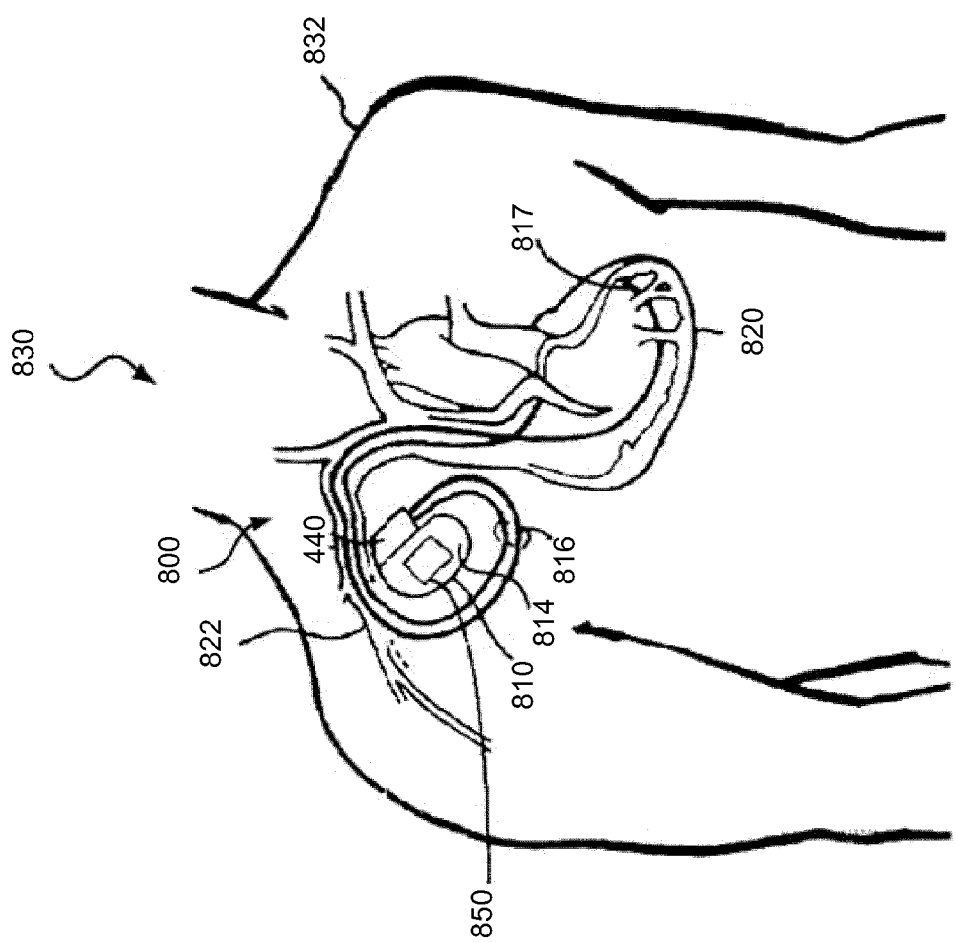
FIG. 19 is a schematic view of a system in the form of an implantable medical device implanted within a body or torso of a patient.
Figure 20:
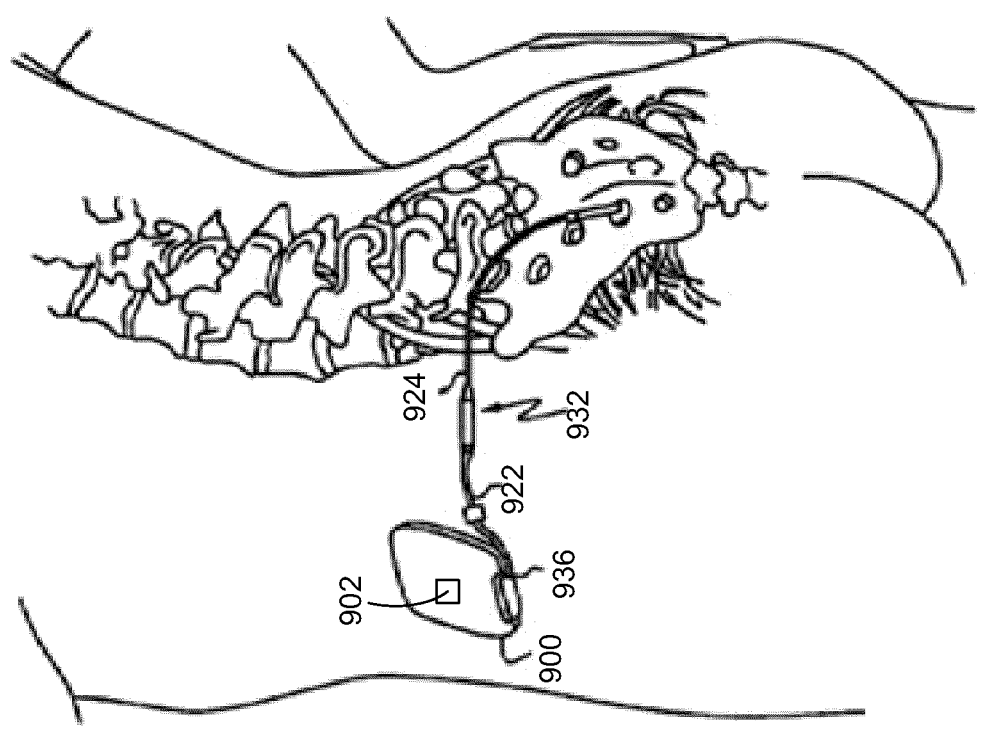
FIG. 20 is schematic view of another system in the form of an implantable medical device.

FIG. 19 illustrates a schematic view of a system 800 (e.g., an implantable medical device) implanted within a body or torso 832 of a patient 830. The system 800 includes a device 810 in the form of an implantable medical device that for purposes of illustration is shown as a defibrillator configured to provide a therapeutic high voltage (e.g., 700 volt) treatment for the patient 830.

The device 810 includes a container or housing 814 that is hermetically sealed and biologically inert according to an exemplary embodiment. The container may be made of a conductive material. One or more leads 816 electrically connect the device 810 and to the patient's heart 820 via a vein 822. Electrodes 817 are provided to sense cardiac activity and/or provide an electrical potential to the heart 820. At least a portion of the leads 816 (e.g., an end portion of the leads shown as exposed electrodes 817) may be provided adjacent or in contact with one or more of a ventricle and an atrium of the heart 820.

The device 810 includes a battery 840 provided therein to provide power for the device 810. According to another exemplary embodiment, the battery 840 may be provided external to the device or external to the patient 830 (e.g., to allow for removal and replacement and/or charging of the battery). The size and capacity of the battery 840 may be chosen based on a number of factors, including the amount of charge required for a given patient's physical or medical characteristics, the size or configuration of the device, and any of a variety of other factors. According to an exemplary embodiment, the battery is a 500 mAh battery. According to another exemplary embodiment, the battery is a 700 mAh battery. According to various other exemplary embodiments, the battery may have a capacity of between approximately 10 and 1000 mAh.

According to other exemplary embodiments, more than one battery may be provided to power the device 810. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

One or more capacitors (shown as capacitor bank 850) are provided in the device to store energy provided by the battery 840. For example, the system 810 may be configured such that when the device 810 determines that a therapeutic high-voltage treatment is required to establish a normal sinus rhythm for the heart 820, the capacitors in the capacitor bank 850 are charged to a predetermined charge level by the battery 840. Charge stored in the capacitors may then be discharged via the leads 816 to the heart 820. According to another exemplary embodiment, the capacitors may be charged prior to determination that a stimulating charge is required by the heart such that the capacitors may be discharged as needed.

According to another exemplary embodiment shown in FIG. 13, an implantable neurological stimulation device 900 (an implantable neuro stimulator or INS) may include a battery 902 such as those described above with respect to the various exemplary embodiments. Examples of other neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 900 includes a lead extension 922 and a stimulation lead 924. The stimulation lead 924 is one or more insulated electrical conductors with a connector 932 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 932 can be connected directly to the INS 900 (e.g., at a point 936), typically the lead connector 932 is connected to a lead extension 922. The lead extension 922, such as a Model 7495 available from Medtronic, is then connected to the INS 900.

Implantation of an INS 900 typically begins with implantation of at least one stimulation lead 924, usually while the patient is under a local anesthetic. The stimulation lead 924 can either be percutaneously or surgically implanted. Once the stimulation lead 924 has been implanted and positioned, the stimulation lead's 924 distal end is typically anchored into position to minimize movement of the stimulation lead 924 after implantation. The stimulation lead's 924 proximal end can be configured to connect to a lead extension 922.

The INS 900 is programmed with a therapy and the therapy is often modified to optimize the therapy for the patient (i.e., the INS may be programmed with a plurality of programs or therapies such that an appropriate therapy may be administered in a given situation). In the event that the battery 902 requires recharging, an external lead (not shown) may be used to electrically couple the battery to a charging device or apparatus.

A physician programmer and a patient programmer (not shown) may also be provided to allow a physician or a patient to control the administration of various therapies. A physician programmer, also known as a console programmer, uses telemetry to communicate with the implanted INS 900, so a clinician can program and manage a patient's therapy stored in the INS 900, troubleshoot the patient's INS 900 system, and/or collect data. An example of a physician programmer is a Model 7432 Console Programmer available from Medtronic. A patient programmer also uses telemetry to communicate with the INS 900, so the patient can manage some aspects of her therapy as defined by the clinician. An example of a patient programmer is a Model 7434 Itrel® 3 EZ Patient Programmer available from Medtronic.

While the medical devices described herein (e.g., systems 800 and 900) are shown and described as a defibrillator and a neurological stimulation device, it should be appreciated that other types of implantable medical devices may be utilized according to other exemplary embodiments, such as pacemakers, cardiac contractility modulators, cardioverters, drug administering devices, diagnostic recorders, cochlear implants, and the like for alleviating the adverse effects of various health ailments. According to still other embodiments, non-implantable medical devices or other types of devices may utilize batteries as are shown and described in this disclosure.

It is also contemplated that the medical devices described herein may be charged or recharged when the medical device is implanted within a patient. That is, according to an exemplary embodiment, there is no need to disconnect or remove the medical device from the patient in order to charge or recharge the medical device. For example, transcutaneous energy transfer (TET) may be used, in which magnetic induction is used to deliver energy from outside the body to the implanted battery, without the need to make direct physical contact to the implanted battery, and without the need for any portion of the implant to protrude from the patient's skin. According to an exemplary embodiment, a connector may be provided external to the patient's body that may be electrically coupled to a charging device in order to charge or recharge the battery. According to other exemplary embodiments, medical devices may be provided that may require removal or detachment from the patient in order to charge or recharge the battery.

It should be understood that while the present disclosure describes the use of lithium-ion batteries with a variety of medical devices, such batteries may be used in a variety of other applications, including computers (e.g., laptop computers), phones (e.g., cellular, mobile, or cordless phones), automobiles, and any other device or application for which it may be advantageous to provide power in the form of a lithium-ion battery.

While the medical devices described herein (e.g., systems 400, 500, 800, and 900) are shown and described as a defibrillator and a neurological stimulation device, it should be appreciated that other types of implantable medical devices may be utilized according to other exemplary embodiments, such as pacemakers, cardioverters, cardiac contractility modulators, drug administering devices, diagnostic recorders, cochlear implants, and the like for alleviating the adverse effects of various health ailments. According to still other embodiments, non-implantable medical devices or other types of devices may utilize batteries as are shown and described in this disclosure.

It is also contemplated that the medical devices described herein may be charged or recharged when the medical device is implanted within a patient. That is, according to an exemplary embodiment, there is no need to disconnect or remove the medical device from the patient in order to charge or recharge the medical device. For example, transcutaneous energy transfer (TET) may be used, in which magnetic induction is used to deliver energy from outside the body to the implanted battery, without the need to make direct physical contact to the implanted battery, and without the need for any portion of the implant to protrude from the patient's skin. According to another exemplary embodiment, a connector may be provided external to the patient's body that may be electrically coupled to a charging device in order to charge or recharge the battery. According to other exemplary embodiments, medical devices may be provided that may require removal or detachment from the patient in order to charge or recharge the battery.

It is also important to note that the construction and arrangement of the lithium-ion battery as shown and described with respect to the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. Other substitutions, modifications, changes and omissions may be made in the design, operating conditions and arrangement of the preferred and other exemplary embodiments without departing from the scope of the present invention as expressed in the appended claims.

What is claimed is:

1. A lithium-ion battery comprising:
   a positive electrode comprising:
      a positive current collector;
      a first material comprising $LiCoO_2$, $LiNiO_2$, or $LiMnO_2$, the first material being an active material; and
      a second material comprising carbon, the second material being conductive; and
   a negative electrode comprising:
      a negative current collector;
      a third material comprising a lithium titanate material, the third material being another active material; and
      a fourth material comprising carbon, the fourth material being conductive;
   a liquid electrolyte; and
   a battery case comprising titanium, at least partially surrounding the positive and negative electrodes;
   wherein the positive electrode and the negative electrode are wound electrodes; and
   wherein a charging and discharging capacity of the positive electrode at a zero voltage crossing potential is below a corrosion potential of the negative current collector and above a decomposition potential of the first material.

2. The lithium-ion battery of claim 1, wherein the first material comprises $LiCoO_2$.

3. The lithium-ion battery of claim 1, wherein the first material comprises $LiNiO_2$.

4. The lithium-ion battery of claim 1, wherein the first material comprises $LiMnO_2$.

5. The lithium-ion battery of claim 1, wherein the positive and negative current collectors comprise a thin foil comprising aluminum.

6. The lithium-ion battery of claim 5, wherein the first material comprises $LiCoO_2$.

7. The lithium-ion battery of claim 6, wherein the fourth material comprises carbon black.

8. The lithium-ion battery of claim 7, further comprising:
   an electrolyte comprising lithium hexafluorophosphate and ethylene carbonate.

9. The lithium-ion battery of claim 8, wherein the positive and negative electrodes further comprise a binder comprising polyvinylidene fluoride.

10. The lithium-ion battery of claim 5, wherein the first material comprises $LiNiO_2$.

11. The lithium-ion battery of claim 5, wherein the first material comprises $LiMnO_2$.

* * * * *